(12) United States Patent
Dixon et al.

(10) Patent No.: US 8,129,592 B2
(45) Date of Patent: Mar. 6, 2012

(54) PLANT ISOFLAVONOID HYDROXYLASES AND METHODS OF USE THEREOF

(75) Inventors: Richard A. Dixon, Ardmore, OK (US); Chang-Jun Liu, San Diego, CA (US)

(73) Assignee: The Samuel Roberts Noble Foundation, Inc., Ardmore, OK (US)

(*) Notice: Subject to any disclaimer, the term of this patent is extended or adjusted under 35 U.S.C. 154(b) by 531 days.

(21) Appl. No.: 12/259,951

(22) Filed: Oct. 28, 2008

(65) Prior Publication Data

US 2009/0142471 A1 Jun. 4, 2009

Related U.S. Application Data

(62) Division of application No. 10/976,190, filed on Oct. 28, 2004, now Pat. No. 7,442,851.

(60) Provisional application No. 60/515,559, filed on Oct. 29, 2003.

(51) Int. Cl.
*C12N 15/29* (2006.01)
*C12N 15/52* (2006.01)
*C12N 15/82* (2006.01)
*A01H 5/00* (2006.01)
*A01H 5/10* (2006.01)

(52) U.S. Cl. .... 800/301; 800/298; 536/23.6; 435/320.1; 435/419

(58) Field of Classification Search .................. 536/23.6; 435/320.1, 419; 800/298, 301
See application file for complete search history.

(56) References Cited

U.S. PATENT DOCUMENTS

| 4,554,101 A | 11/1985 | Hopp .................. 260/999.999 |
| 2004/0093632 A1 | 5/2004 | Dixon et al. ............... 800/278 |
| 2006/0123508 A1 | 6/2006 | Dixon et al. ............... 800/278 |

FOREIGN PATENT DOCUMENTS

| WO | WO 00/37652 | 6/2000 |
| WO | WO 02/066625 | 8/2002 |
| WO | WO 03/031622 | 4/2003 |
| WO | WO 03/040306 | 5/2003 |
| WO | WO 03/093464 | 11/2003 |
| WO | WO 2004/090136 | 10/2004 |

OTHER PUBLICATIONS

Liu C. et al. PNAS, 2002, vol. 99, No. 22; pp. 14578-14583.*
Overkamp, S. et al. Plant Science (2000) vol. 155; pp. 101-108.*
Urban, P. et al. Eur. J. of Biochemistry (1994) vol. 222; pp. 843-850.*
Blast Basic Local Alignment Search Tool, Job Title: Icl|4054 (498 letters), dated Sep. 19, 2008.
Blast Basic Local Alignment Search Tool, Job Title: Nucleotide Sequence (1560 letters), dated Sep. 19, 2008.
GenPept Accession No. Q9XFX0, dated Nov. 28, 2006.
GenPept Accession No. Q9ZRW6, dated Nov. 28, 2006.
Akashi et al., "CYP81E1, a Cytochrome P450 cDna of Licorice (Glycyrrhiza echinata L.) Encodes isoflavone 2'-hydroxylase," *Biochemical and Biophysical Research Communications*, 251:67-70, 1998.
Bhandari et al., "Biosynthesis of the A/B/C/D-ring system of the rotenoid amorphigenin by Amorpha fruticosa seedlings," *J. Chem. Soc. Perkin Trans.*, 839-849, 1992.
Choudhary et al., "Stress responses in alfalfa (Medicago sativa L.) IV. Expression of defense gene constructs in electroporated suspension cell photoplasts," *Plant Cell Rep.*, 9:42-46, 1990.
Clemens et al., "Cytochrome P450-dependant methylenedioxy bridge formation in Cicer Arietinum," *Phytochemistry*, 41:457-460, 1996.
Clemens et al., "Characterization of Cytochrome P450-dependent isoflavone hydroxylasas from chickpea," *Phytochemistry*, 32:653-657, 1993.
Dewick, "Isoflavonoids," *The Flavonoids: Advances in Research Since 1986.*, Harborne (Ed.), London: Chapman and Hall, 117-238, 1993.
Dixon et al., "Molecules of Interest Genistein," *Phytochemistry*, 60:205-211, 2002.
Dixon et al., "Legume natural products: understanding and manipulating complex pathways for human and animal health," *Plant Physiol.*, 131:878-885, 2003.
Dixon et al., "The phenylpropanoid pathway and plant defence—a genomics perspective," *Mol. Plant Pathol.*, 3:371-390, 2002.
Dixon, "Isoflavonoids: biochemistry, molecular biology, and biological functions," *Comprehensive Natural Products Chemistry*, Barton et al. (ed), Elsevier, 1:773-823, 1999.
GenBank Accession No. AB001379.
GenBank Accession No. AB022732.
GenBank Accession No. AB025016.
GenBank Accession No. AJ012581.
GenBank Accession No. AJ238439.
GenBank Accession No. AY166658.
GenBank Accession No. AY278227.
GenBank Accession No. AY278229.
Gunia et al., "Elicitor induction of cytochrome P450 monooxygenases in cell suspension cultures of chickpea (Cicer arietinum L.) and their involvement in pterocarpan phytoalexin biosynthesis," *Z. Naturforsch.* 46:58-66, 1991.
Hahn et al., "ESTs from roots of Medicago truncatula treated with oligogalacturonides of DP 6-20," 2001, Accession No. BG648057.
He et al., "Genetic manipulation of isoflavone 7-O-methyltransferase enhances biosynthesis of 4'0-methylated isoflavonoid phytoalexins and disease resistance in alfalfa," *Plant Cell*, 12:1689-1702, 2000.
Hinderer et al., "Microsomal isoflavone 2'- and 3'-hydroxylases from chickpea (Cicer arietinum L.) cell suspensions induced for pterocarpan phytoalexin formation," *Febs Letters*, 214:101-106, 1987.

(Continued)

*Primary Examiner* — Russell Kallis
(74) *Attorney, Agent, or Firm* — SNR Denton US LLP

(57) ABSTRACT

The invention provides plant isoflavonoid hydroxylase coding sequences. Also provided are constructs comprising these sequences, plants transformed therewith and methods of use thereof. In certain aspects of the invention, plants transformed with the nucleic acids are provided exhibiting improved pest and disease resistance. Plants provided by the invention may also exhibit improved nutritional qualities.

18 Claims, 6 Drawing Sheets

OTHER PUBLICATIONS

Kochs et al., "Phytoalexin synthesis in soybean: purification and reconstitution of cytochrome P450 3,9-dihydroxypterocarpan 6a-hydroxylase and separation from Cytochrome P450 cinnamate 4-hydroxylase," *Arch. Biochem. Biophys.*, 273:543-553, 1989.

Lambert et al., "Production of rotenoids by heterotrophic and photomixotrophic cell cultures of tephrosia vogelii," *Phytochemistry*, 34:1515-1520, 1993.

LatundeDada et al., "Flavonoid 6-hydroxylase from soybean (Glycine max. L.), a novel plant P-450 monooxygenase," *J. Biol. Chem.*, 276:1688-1695, 2001.

Liu et al., "Elicitor-induced association of isoflavone O-methyltransferase with endomembranes prevents the formation and 7-O-methylation of daidzein during isoflavonoid phytoalexin biosynthesis," *Plant Cell*, 13:2643-2658, 2001.

Liu et al., "Bottlenecks for metabolic engineering of isoflavone glycocojugates in Arabidopsis," *Proc. Natl. Acad. Sci USA*, 99:14578-14583, 2002.

Liu et al., "Regiospecific hydroxylation of isoflavones by ctyochrome P450 81E enzymes from medicago truncatula," *The Plant Journal*, 36:471-484, 2000.

Mackenbrock et al., "3'-Hydroxylation of 4'-Methoxyisoflavones by Fusarium oxysporum f. lycopersici," *Z. Naturforsch.* 38:708-710, 1983.

Mackenbrock et al., "Accumulation and metabolism of medicarpin and maackiain maolnylgucosides in elicited chickpea (Cicer arietinum L.) cell suspension cultures," *J. Plant Physiol.*, 142:385-391, 1993.

Mihaliak et al., "Cytochrome P450 terpene hydroxylases," *Meth. Plant Biochem.*, 9:261-279, 1993.

Nakamura et al., "Induction of isoflavonoid and retrochalcone branches of the flavonoid pathway in cultured Glycyrrhiza echinata cells treated with yeast extract," *Biosci. Biotechnol. Biochem.*, 63:1618-1620, 1999.

Overkamp et al., "Cloning of two cicer arietinum L. cDNA's encoding Cytochrome P450's highly homologous Isoflavone 2'-Hydroxylase from licorice," *Plant Physiol.*, 120:935, 1999.

Overkamp et al., Cloning and characterization of eight cytochrome P450 cDNAs from chickpea (Cicer arietinum L.) cell suspension cultures, *Plant Science*, 155:101-108, 2000.

Pompon et al., "Yeast expression of animal and plant P450s in optimized redox environments," *Meth. Enzymol.*, 272:51-64, 1996.

Shimada et al., "Induction of isoflavonoid pathway in the model legume Lotus japonicus: molecular characterization of enzymes involved in phytoalexin biosynthesis," *Plant Science*, 160:37-47, 2000.

Simmonds et al., "Effects of isoflavonoids from Cicer on larve of Heliocoverpa armigera," *J. Chem. Ecol.*, 27:965-977, 2001.

Tebayashi et al., "Elicitor-induced changes in isoflavonoid metabolism in red clover roots," *J. Exp. Bot.*, 52:681-668, 2001.

Tolleson et al., "Metabolism of Biochanin A and formononetin by human liver microsomes in vitro," *J. Agric. Food Chem.*, 50:4783-4790, 2002.

\* cited by examiner

SEQUENCE LISTING

```
<160> NUMBER OF SEQ ID NOS: 21

<210> SEQ ID NO 1
<211> LENGTH: 1560
<212> TYPE: DNA
<213> ORGANISM: Medicago truncatula

<400> SEQUENCE: 1
actcattctc caaataacaa tttaaggtag ccaaaaccaa attaattagt aattaacaaa      60
ctcaaccatg gggatccttt cctatttgtg ctactctctc ttttatcttt ctatattttt     120
catcattagg cttttgttcc aatcaagaaa attcaaaaac cttccaccag gtccaacttc     180
tcttcctata attggtaacc ttcaccatct caaacgtccc ctaaaccgta cctttaaggc     240
actcactgaa aagtatggta acgtgatttc cctttggttt ggttcacgtc ttgttgtcgt     300
tgtttcttca cttccgaatt tcaagaatg ttttacaaaa aacgacgttg tcctagcaaa      360
tagaccacgg tttttatccg gaaatatat tttctacaat tacaccactt taggatctac      420
ctcctacggt gaacactggc gtaaccttcg tcgtatcact tcccttgatg ttctttcaaa     480
ccaccgtatc aacaactttg ctcctatccg aagagacgag actcagaggt tgatcaagaa     540
gttggctgaa gattcatcca ctaaatttgc tgaagtagaa cttactttca ggtttttcga     600
tatgaccttc aacaacatca tgagaatgat ctctggaaag agatactatg gtgatgattg     660
cgacatatct gaggttcaag aagcaagtca atttagggat atggtatctg aactgttgca     720
gttatcagga gcaaacaata agactgattt catgcccttg ttaaagtttc ttgactttga     780
aaacttggag aagagagtca agcgtattgg tgaaaagaat gatgtatttt tgagtggact     840
ccttcaagag caacgtagca agaaagaacg tacaaatacc atgatagatc atcttctaaa     900
catgcaagaa tcacagccag agtactacac cgatacaatc atcaaaggcc tttgtttggc     960
aatgctcctt gctggaacgg actcatctgc cgtaacatta gagtggacca tgtcaaatat    1020
tttgaactat ccagaggtat tgaaaaaggt aagagatgaa gtggatactc atgtaggaca    1080
agatcgtttg gttgatgaat cagaccttcc gaaactaact tacctaagaa atgttatcta    1140
cgagacccct cgattgtata ctcctgctcc attgttatta ccacactcaa ctgcagatga    1200
gtgcattatg ggaggataca aagttccgcg cgacaccata gtattgatca atgcttgggc    1260
```

-continued

```
cattcataga gaccctgaaa catggagtga agccacaact ttcaagccgg agaggttcga    1320
caaaaaagga gagttggaga agatgattgc atttggaatg ggaagaaggg catgtccagg    1380
agaaggttta gctcttcgag caattagcat gacattggca ttattggttc aatgctttga    1440
ttggaaacgt ataaacgatg aaaaaattga tatgtcagaa cgagatgggt tcactatgac    1500
aaagttacta ccattgaagg ccatgtgtaa aactcgtccg gtcgtcaaca aggttttcaa    1560
```

<210> SEQ ID NO 2
<211> LENGTH: 498
<212> TYPE: PRT
<213> ORGANISM: Medicago truncatula

<400> SEQUENCE: 2

```
Met Gly Ile Leu Ser Tyr Leu Cys Tyr Ser Leu Phe Tyr Leu Ser Ile
1               5                   10                  15

Phe Phe Ile Ile Arg Leu Leu Phe Gln Ser Arg Lys Phe Lys Asn Leu
            20                  25                  30

Pro Pro Gly Pro Thr Ser Leu Pro Ile Ile Gly Asn Leu His His Leu
        35                  40                  45

Lys Arg Pro Leu Asn Arg Thr Phe Lys Ala Leu Thr Glu Lys Tyr Gly
    50                  55                  60

Asn Val Ile Ser Leu Trp Phe Gly Ser Arg Leu Val Val Val Val Ser
65                  70                  75                  80

Ser Leu Ser Glu Phe Gln Glu Cys Phe Thr Lys Asn Asp Val Leu
                85                  90                  95

Ala Asn Arg Pro Arg Phe Leu Ser Gly Lys Tyr Ile Phe Tyr Asn Tyr
            100                 105                 110

Thr Thr Leu Gly Ser Thr Ser Tyr Gly Glu His Trp Arg Asn Leu Arg
        115                 120                 125

Arg Ile Thr Ser Leu Asp Val Leu Ser Asn His Arg Ile Asn Asn Phe
    130                 135                 140

Ala Pro Ile Arg Arg Asp Glu Thr Gln Arg Leu Ile Lys Lys Leu Ala
145                 150                 155                 160

Glu Asp Ser Ser Thr Lys Phe Ala Glu Val Glu Leu Thr Phe Arg Phe
                165                 170                 175

Phe Asp Met Thr Phe Asn Asn Ile Met Arg Met Ile Ser Gly Lys Arg
            180                 185                 190

Tyr Tyr Gly Asp Asp Cys Asp Ile Ser Glu Val Gln Glu Ala Ser Gln
        195                 200                 205

Phe Arg Asp Met Val Ser Glu Leu Leu Gln Leu Ser Gly Ala Asn Asn
    210                 215                 220

Lys Thr Asp Phe Met Pro Leu Leu Lys Phe Leu Asp Phe Glu Asn Leu
225                 230                 235                 240

Glu Lys Arg Val Lys Arg Ile Gly Glu Lys Asn Asp Val Phe Leu Ser
                245                 250                 255

Gly Leu Leu Gln Glu Gln Arg Ser Lys Lys Glu Arg Thr Asn Thr Met
            260                 265                 270

Ile Asp His Leu Leu Asn Met Gln Glu Ser Gln Pro Glu Tyr Tyr Thr
        275                 280                 285

Asp Thr Ile Ile Lys Gly Leu Cys Leu Ala Met Leu Leu Ala Gly Thr
    290                 295                 300

Asp Ser Ser Ala Val Thr Leu Glu Trp Thr Met Ser Asn Ile Leu Asn
305                 310                 315                 320

Tyr Pro Glu Val Leu Lys Lys Val Arg Asp Glu Val Asp Thr His Val
```

```
            325                 330                 335
Gly Gln Asp Arg Leu Val Asp Glu Ser Asp Leu Pro Lys Leu Thr Tyr
            340                 345                 350

Leu Arg Asn Val Ile Tyr Glu Thr Leu Arg Leu Tyr Thr Pro Ala Pro
            355                 360                 365

Leu Leu Leu Pro His Ser Thr Ala Asp Glu Cys Ile Met Gly Gly Tyr
            370                 375                 380

Lys Val Pro Arg Asp Thr Ile Val Leu Ile Asn Ala Trp Ala Ile His
385                 390                 395                 400

Arg Asp Pro Glu Thr Trp Ser Glu Ala Thr Thr Phe Lys Pro Glu Arg
                405                 410                 415

Phe Asp Lys Lys Gly Glu Leu Glu Lys Met Ile Ala Phe Gly Met Gly
                420                 425                 430

Arg Arg Ala Cys Pro Gly Glu Gly Leu Ala Leu Arg Ala Ile Ser Met
                435                 440                 445

Thr Leu Ala Leu Leu Val Gln Cys Phe Asp Trp Lys Arg Ile Asn Asp
            450                 455                 460

Glu Lys Ile Asp Met Ser Glu Arg Asp Gly Phe Thr Met Thr Lys Leu
465                 470                 475                 480

Leu Pro Leu Lys Ala Met Cys Lys Thr Arg Pro Val Val Asn Lys Val
                485                 490                 495

Phe Lys

<210> SEQ ID NO 3
<211> LENGTH: 1577
<212> TYPE: DNA
<213> ORGANISM: Medicago truncatula

<400> SEQUENCE: 3
gttacccata atcaacaaaa aaatgactac tttctatctc tcactcatca tctctctctt      60
tttccttatc atcactttga aggtcttctt caatacttca agaaagttca aaaaccttcc    120
accaggccca caatgtcttc ctataattgg aaaccttcac caactcaaac aaccactcca    180
ccacacattc cacaccttat cacaaaaata tggccaaatc ttttctcttt ggttcggttc    240
tcgtctcgtc gttgttgttt catcgttaac aatagcacaa gaatgtttta ccaaaaacga    300
catagtttta gcgaaccgac tcatttctt aactggaaaa tatattggct acaacaatac    360
tacggtagca caatcacctt atggtgacca ttggcgcaat cttcgacgaa tattatcaat    420
tgaaatactc tcatctcatc gtttaaattc cttcttggaa atacgaagag atgagattat    480
gagactaata caaaagctag cacaaaaatc atacaatggt ttcaccgaag tggaacttag    540
acctatgttt tcgaaatga catttaatac tataatgaga atggtgtcgg ggaaaagata    600
ctatggaaat gattgtgatg tgagtgatgt tgaggaagca aggttgttta gagggataat    660
taaagaggtt gttagtttag gaggagctaa caacgttggt gattttttgg ttttttaag     720 gtggtttgat tttgatggtt tggaaaagag gcttaagaag attagtaaga gaaccgatgc    780 attttttacaa gggcttattg atgaacatcg ttttggaaag aggaatagta acactatgat    840
tgatcatctc ttaacacagc aacaatcaca acccgaatat tatacggacc aaatcatcaa    900
aggacttatg gtggttatgt tacttgcggg aacagacaca tcatccgtaa caatagaatg    960
ggctatgtcc aatttactaa accatccaga aataatgaag aaggcaaaaa atgagttgga   1020
cacccatata ggacatgatc gccaagtaga tgagcatgac atttcaaaac ttccttatct   1080
tcaaagcatt gtctatgaaa cccttcgact acatgcagca gctccattat tagtgcctca   1140
```

```
tttgtcatca gaagattttt ccttaggagg atataatatc ccacaaaaca caattttgat    1200
ggtgaatgct tgggtcattc atagagatcc aaatttgtgg agtgatccta cttgttttaa    1260
gccagagagg tttgagaaag aaggtgaggt gaataaatta ctttcatttg ggttgggtag    1320
aagggcttgt ccaggagaaa acttatccca aaggactgag ggcttgactt tgggcttatt    1380
gattcagtgt tttgagtgga aacgaatagg tgaagaaaaa attgacatgg ttgaagcaaa    1440
agggatcacg gcgggaaaaa agacttcctt aaatgcaatg tgtaaagtgc gacatccatt    1500
gaagattaac gatgttttttt agtttttatt aatgttcgag attcgttgaa acatgcaca    1560 tgatgcaaac atgttga                                                  1577

<210> SEQ ID NO 4
<211> LENGTH: 499
<212> TYPE: PRT
<213> ORGANISM: Medicago truncatula

<400> SEQUENCE: 4

Met Thr Thr Phe Tyr Leu Ser Leu Ile Ile Ser Leu Phe Phe Leu Ile
1               5                   10                  15

Ile Thr Leu Lys Val Phe Phe Asn Thr Ser Arg Lys Phe Lys Asn Leu
            20                  25                  30

Pro Pro Gly Pro Gln Cys Leu Pro Ile Ile Gly Asn Leu His Gln Leu
        35                  40                  45

Lys Gln Pro Leu His His Thr Phe His Thr Leu Ser Gln Lys Tyr Gly
    50                  55                  60

Gln Ile Phe Ser Leu Trp Phe Gly Ser Arg Leu Val Val Val Val Ser
65                  70                  75                  80

Ser Leu Thr Ile Ala Gln Glu Cys Phe Thr Lys Asn Asp Ile Val Leu
                85                  90                  95

Ala Asn Arg Pro His Phe Leu Thr Gly Lys Tyr Ile Gly Tyr Asn Asn
            100                 105                 110

Thr Thr Val Ala Gln Ser Pro Tyr Gly Asp His Trp Arg Asn Leu Arg
        115                 120                 125

Arg Ile Leu Ser Ile Glu Ile Leu Ser Ser His Arg Leu Asn Ser Phe
    130                 135                 140

Leu Glu Ile Arg Arg Asp Glu Ile Met Arg Leu Ile Gln Lys Leu Ala
145                 150                 155                 160

Gln Lys Ser Tyr Asn Gly Phe Thr Glu Val Glu Leu Arg Pro Met Phe
                165                 170                 175

Ser Glu Met Thr Phe Asn Thr Ile Met Arg Met Val Ser Gly Lys Arg
            180                 185                 190

Tyr Tyr Gly Asn Asp Cys Asp Val Ser Asp Val Glu Glu Ala Arg Leu
        195                 200                 205

Phe Arg Gly Ile Ile Lys Glu Val Val Ser Leu Gly Gly Ala Asn Asn
    210                 215                 220

Val Gly Asp Phe Leu Gly Phe Leu Arg Trp Phe Asp Phe Asp Gly Leu
225                 230                 235                 240

Glu Lys Arg Leu Lys Lys Ile Ser Lys Arg Thr Asp Ala Phe Leu Gln
                245                 250                 255

Gly Leu Ile Asp Glu His Arg Phe Gly Lys Arg Asn Ser Asn Thr Met
            260                 265                 270

Ile Asp His Leu Leu Thr Gln Gln Ser Gln Pro Glu Tyr Tyr Thr
        275                 280                 285

Asp Gln Ile Ile Lys Gly Leu Met Val Val Met Leu Leu Ala Gly Thr
    290                 295                 300
```

```
Asp Thr Ser Ser Val Thr Ile Glu Trp Ala Met Ser Asn Leu Leu Asn
305                 310                 315                 320

His Pro Glu Ile Met Lys Lys Ala Lys Asn Glu Leu Asp Thr His Ile
            325                 330                 335

Gly His Asp Arg Gln Val Asp Glu His Asp Ile Ser Lys Leu Pro Tyr
        340                 345                 350

Leu Gln Ser Ile Val Tyr Glu Thr Leu Arg Leu His Ala Ala Ala Pro
    355                 360                 365

Leu Leu Val Pro His Leu Ser Ser Glu Asp Phe Ser Leu Gly Gly Tyr
370                 375                 380

Asn Ile Pro Gln Asn Thr Ile Leu Met Val Asn Ala Trp Val Ile His
385                 390                 395                 400

Arg Asp Pro Asn Leu Trp Ser Asp Pro Thr Cys Phe Lys Pro Glu Arg
            405                 410                 415

Phe Glu Lys Glu Gly Glu Val Asn Lys Leu Leu Ser Phe Gly Leu Gly
        420                 425                 430

Arg Arg Ala Cys Pro Gly Glu Asn Leu Ser Gln Arg Thr Glu Gly Leu
    435                 440                 445

Thr Leu Gly Leu Leu Ile Gln Cys Phe Glu Trp Lys Arg Ile Gly Glu
450                 455                 460

Glu Lys Ile Asp Met Val Glu Ala Lys Gly Ile Thr Ala Gly Lys Lys
465                 470                 475                 480

Thr Ser Leu Asn Ala Met Cys Lys Val Arg His Pro Leu Lys Ile Asn
            485                 490                 495

Asp Val Phe

<210> SEQ ID NO 5
<211> LENGTH: 1868
<212> TYPE: DNA
<213> ORGANISM: Medicago truncatula

<400> SEQUENCE: 5
gccttattct attactctct cctttctcta tccttcatca taaccatcaa aattttactc    60
aaaatcacat caagaaggct aaaaaacctt ccaccaggtc caccaacaat tcctataatt   120
ggcaacctcc accacctaaa acaccctctc caccgtacct tcaaccccct atcacaaaca   180
tacggtgaca tcttttcact ttggttcggt tcgcgcctag ttgtcgttgt ttcttccccg   240
tctttagccc atgaatgctt cacaaaaaac gacatcattt tagcgaaccg accacgtttc   300
ctaaccggaa aatacatctt ttacaattac acaaccctag gctccgcttc ttatggggac   360
cattggcgta atctacgtcg tataacaacc attgatgttc tttctaacaa tcgtcttaac   420
tccttcttag gagttcgaag agacgaaaca aatagactta tacaaaagct tctcaaagac   480
gtcgtctctg aaggtttcgg tttcactaaa gtggaactga gaccgagact aacagagatg   540
acgtttaatg ctatgatgag aatgatatcg ggaaaacggt attatggaga tgacggagat   600
gtgtcagatg ttgaagaagc taaacaattt agggagataa taagtgagat gatgtctttg   660
ttaggtgcta ataataaggg tgattttttg cctttgttaa gggtggttga tcttgataat   720
ttggagaaaa ggtgcaagag gattgcaaaa agatctaatg cattttttgga gggactcatt   780
gaggaacatc gccgtggaaa tattcatagt gatggaggta caatgattga tcatcttttg   840
aagctaagtg aatcacaacc tgagtattat tcagatcatt tgatcaaagg tctaattcag   900
ggtatgcttc ttgcgggaac agacacatca gcagtgacaa tagaatgggt aatgtctgaa   960
ttgttgaacc acccagaagt attaaagaaa gcaaagaag aattagacac tcaaattgga   1020
```

```
aaaaacaaat tagtagatga acaagatttg tcaaaacttc catacctaca aacataatc   1080 tctgaaacac ttagattgca tccaccagct ccactacttt tgccacatta ttcttcagag   1140
gattgcacta ttggagaatt caatgttcca aaagatacta taatattgac caatgtttgg   1200
ggtattcata gagatccaaa acattggaat gatgctttga gttttaaacc agagaggttt   1260 gaaaagaag aggaggtgaa caaagtaatg gcatttgggt taggaagaag ggcttgtcct    1320
ggattaagct tggcccaacg tactgtgggc tttactgtgg gcttgttgat ccaatgcttt   1380
gaatgggaaa gagagagtga ggaaaaactt gatatgatgg agggtaaagg aattaccatg   1440
ccaatgaaga taccattaag ggctatgtgt aaagcactac ctatagccaa tgatgtaacg   1500
aagtgagaga aatgttatga ataccctctt tttagcattc tttctaatac tcgttttttt   1560
attgggtgaa actcatataa gtctcactat tttatgtgag atccattttc aatgtgtagt   1620
atccacataa atttcatcca ataaacaagt gggtgttaga aaaacgtta gaaagagatt    1680 gtgtatagca ctcctcgatg aagtgatgcc ctttttggt tacatccaat gataacttat     1740
ctctcagcta gtagaaattg tgtgacgata taatgatatg taaattagac tctattttc    1800 tccctctata ttatgctctc ctttacttca gagaaagcta ccttatattt aaaaaaaaa   1860 aaaaaaaa                                                            1868

<210> SEQ ID NO 6
<211> LENGTH: 501
<212> TYPE: PRT
<213> ORGANISM: Medicago truncatula

<400> SEQUENCE: 6

Ala Leu Phe Tyr Tyr Ser Leu Leu Ser Leu Ser Phe Ile Ile Thr Ile
1               5                   10                  15

Lys Ile Leu Leu Lys Ile Thr Ser Arg Arg Leu Lys Asn Leu Pro Pro
            20                  25                  30

Gly Pro Pro Thr Ile Pro Ile Ile Gly Asn Leu His His Leu Lys His
        35                  40                  45

Pro Leu His Arg Thr Phe Thr Thr Leu Ser Gln Thr Tyr Gly Asp Ile
    50                  55                  60

Phe Ser Leu Trp Phe Gly Ser Arg Leu Val Val Val Ser Pro
65                  70                  75                  80

Ser Leu Ala His Glu Cys Phe Thr Lys Asn Asp Ile Ile Leu Ala Asn
                85                  90                  95

Arg Pro Arg Phe Leu Thr Gly Lys Tyr Ile Phe Tyr Asn Tyr Thr Thr
            100                 105                 110

Leu Gly Ser Ala Ser Tyr Gly Asp His Trp Arg Asn Leu Arg Arg Ile
        115                 120                 125

Thr Thr Ile Asp Val Leu Ser Asn Asn Arg Leu Asn Ser Phe Leu Gly
    130                 135                 140

Val Arg Arg Asp Glu Thr Asn Arg Leu Ile Gln Lys Leu Leu Lys Asp
145                 150                 155                 160

Val Val Ser Glu Gly Phe Gly Phe Thr Lys Val Glu Leu Arg Pro Arg
                165                 170                 175

Leu Thr Glu Met Thr Phe Asn Ala Met Met Arg Met Ile Ser Gly Lys
            180                 185                 190

Arg Tyr Tyr Gly Asp Asp Gly Asp Val Ser Asp Val Glu Glu Ala Lys
        195                 200                 205

Gln Phe Arg Glu Ile Ile Ser Glu Met Met Ser Leu Leu Gly Ala Asn
    210                 215                 220
```

```
Asn Lys Gly Asp Phe Leu Pro Leu Leu Arg Val Val Asp Leu Asp Asn
225                 230                 235                 240

Leu Glu Lys Arg Cys Lys Arg Ile Ala Lys Arg Ser Asn Ala Phe Leu
            245                 250                 255

Glu Gly Leu Ile Glu Glu His Arg Arg Gly Asn Ile His Ser Asp Gly
            260                 265                 270

Gly Thr Met Ile Asp His Leu Leu Lys Leu Ser Glu Ser Gln Pro Glu
        275                 280                 285

Tyr Tyr Ser Asp His Leu Ile Lys Gly Leu Ile Gln Gly Met Leu Leu
    290                 295                 300

Ala Gly Thr Asp Thr Ser Ala Val Thr Ile Glu Trp Val Met Ser Glu
305                 310                 315                 320

Leu Leu Asn His Pro Glu Val Leu Lys Lys Ala Lys Glu Glu Leu Asp
                325                 330                 335

Thr Gln Ile Gly Lys Asn Lys Leu Val Asp Glu Gln Asp Leu Ser Lys
            340                 345                 350

Leu Pro Tyr Leu Gln Asn Ile Ile Ser Glu Thr Leu Arg Leu His Pro
        355                 360                 365

Pro Ala Pro Leu Leu Leu Pro His Tyr Ser Ser Glu Asp Cys Thr Ile
370                 375                 380

Gly Glu Phe Asn Val Pro Lys Asp Thr Ile Ile Leu Thr Asn Val Trp
385                 390                 395                 400

Gly Ile His Arg Asp Pro Lys His Trp Asn Asp Ala Leu Ser Phe Lys
                405                 410                 415

Pro Glu Arg Phe Glu Lys Glu Glu Val Asn Lys Val Met Ala Phe
            420                 425                 430

Gly Leu Gly Arg Arg Ala Cys Pro Gly Leu Ser Leu Ala Gln Arg Thr
        435                 440                 445

Val Gly Phe Thr Val Gly Leu Leu Ile Gln Cys Phe Glu Trp Glu Arg
    450                 455                 460

Glu Ser Glu Glu Lys Leu Asp Met Met Glu Gly Lys Gly Ile Thr Met
465                 470                 475                 480

Pro Met Lys Ile Pro Leu Arg Ala Met Cys Lys Ala Leu Pro Ile Ala
                485                 490                 495

Asn Asp Val Thr Lys
            500

<210> SEQ ID NO 7
<211> LENGTH: 23
<212> TYPE: DNA
<213> ORGANISM: Artificial Sequence
<220> FEATURE:
<223> OTHER INFORMATION: Synthetic Primer

<400> SEQUENCE: 7
aacggatcca tgggaatcct ttc                                       23

<210> SEQ ID NO 8
<211> LENGTH: 23
<212> TYPE: DNA
<213> ORGANISM: Artificial Sequence
<220> FEATURE:
<223> OTHER INFORMATION: Synthetic Primer

<400> SEQUENCE: 8
gaacggtacc ttagatgaat tac                                       23
```

```
<210> SEQ ID NO 9
<211> LENGTH: 29
<212> TYPE: DNA
<213> ORGANISM: Artificial Sequence
<220> FEATURE:
<223> OTHER INFORMATION: Synthetic Primer

<400> SEQUENCE: 9
aacggatcca tgaccttatt ctattactc                                       29

<210> SEQ ID NO 10
<211> LENGTH: 26
<212> TYPE: DNA
<213> ORGANISM: Artificial Sequence
<220> FEATURE:
<223> OTHER INFORMATION: Synthetic Primer

<400> SEQUENCE: 10
aacaggtacc tcacttcgtt acatca                                          26

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
caaacggtac catggggatc                                                 20

<210> SEQ ID NO 12
<211> LENGTH: 22
<212> TYPE: DNA
<213> ORGANISM: Artificial Sequence
<220> FEATURE:
<223> OTHER INFORMATION: Synthetic Primer

<400> SEQUENCE: 12
atgaggtacc ttgaaaacct tg                                              22

<210> SEQ ID NO 13
<211> LENGTH: 28
<212> TYPE: DNA
<213> ORGANISM: Artificial Sequence
<220> FEATURE:
<223> OTHER INFORMATION: Synthetic  Primer

<400> SEQUENCE: 13
gacggtacca tgaccttatt ctattact                                        28

<210> SEQ ID NO 14
<211> LENGTH: 28
<212> TYPE: DNA
<213> ORGANISM: Artificial Sequence
<220> FEATURE:
<223> OTHER INFORMATION: Synthetic Primer

<400> SEQUENCE: 14
gacggatcct tcgttacatc attggcta                                        28

<210> SEQ ID NO 15
<211> LENGTH: 1707
<212> TYPE: DNA
<213> ORGANISM: Pisum sativum

<400> SEQUENCE: 15
aacccaacaa aaagtgttaa aaaaatgtca cctttattct attactcttt cctctctcta     60
```

-continued

```
accttcataa taaccatcaa aattttactc caaacccaat caagaaggct aaaaaacctt    120
ccaccaggtc caccaacaat ccccataatt ggcaacctcc accacctaaa acaccctctc    180
caccgtacct tcgcaacctt gtcccaaaaa tacggcgaca tcgtttccct ttggttcggt    240
tcgcgcctag ttgtcgtcat ctcttcggct tctttagtcg aggaatgttt catcaaaaac    300
gacgtcgttt tagcaaaccg cccacgcttc ttaacaggaa aatacatctt ctacgactac    360
accaccttag ggtcagtttc ttacggggac cattggcgta acctacgccg tataacaacc    420
attgatgttc tctctaacaa ccgtcttacc tcttttttgg gagttcggac agacgaagca    480
aatagactta tacaaaatat tataaagcat ggggcttcta gagattttat caaagtggaa    540
ctccggtcga tactgacgga gatgacgttt aatggtatga tgagaatgat atcgggaaaa    600
cggtattacg gagacgacgg agacgtgacg gaagtcgaag aagctaaaca gtttagggaa    660
ataataagtg agatattgtc gctgttaggt gctaataaca agggtgactt tttgcctttg    720
ttaaggtggt ttgatcttga tgatttggag aagaggtgca agaaaattgc aaacagagct    780
gatgcatttt tggaaggact cattcaagaa catcgcagcg cgaatcatgg taatggagat    840
accatgattg atcatctttt gaagcttagt gaggtgcagc tgaatattat tccttctcac    900
atcatcaaag gtcttattca ggccatgctt cttgcaggaa cggacacatc agcactagct    960
atagaatggg tgatgtctga attattaaac catccagaag tgttgaacaa agcaaaggaa   1020
gaaatagaga ctcaagttgg aaaaaacaag ataatagatg aacaagattt accaaaactt   1080
ccatatctcc aaaacataat ctctgaggca cttaagttac atccaccagc accattactt   1140
ttaccacatt attcttcaga ggattgtacc attggaggat tcaatgttcc aaaagatact   1200
ataattttga ctaatgtttg ggccattcat agagatccaa cacgttggag tgatgctttg   1260
agttttaagc cagagaggtt tgaaaagaa ggggaagtga acaaattgat ggcgtttggg   1320
ataggaagaa gagcctgtcc tggattgagc ttggctcaac gtacggtggg gcttaactgt   1380
ggggcttgtt ggttccaatg ctttgagtgg aaaagagaga gtgaggagaa acttgatatg   1440
atggagggta agtattgcc atgccttaaa agatccccat ttaaggctct gtgtaaaggc   1500
acaaccctat tgcccaatga ccttatgaag tgatgagtga attgcatctt ttttttccctt  1560
ctacttgagg agaagctagc ttgaatgttg tattttatat ggatatgtca aactctaagc   1620
tatctaatat tgagaataaa ctatgtattt taataagttt gctttaatat taaatattaa   1680
gctttgtatg cgaaaaaaaa aaaaaaa                                       1707
```

<210> SEQ ID NO 16
<211> LENGTH: 1577
<212> TYPE: DNA
<213> ORGANISM: Medicago truncatula

<400> SEQUENCE: 16

```
gttacccata atcaacaaaa aaatgactac tttctatctc tcactcatca tctctctctt     60
tttccttatc atcactttga aggtcttctt caatacttca agaaagttca aaaaccttcc    120
accaggccca caatgtcttc ctataattgg aaaccttcac caactcaaac aaccactcca    180
ccacacattc cacaccttat cacaaaaata tggccaaatc ttttctcttt ggttcggttc    240
tcgtctcgtc gttgttgttt catcgttaac aatagcacaa gaatgtttta ccaaaaacga    300
catagtttta gcgaaccgac ctcatttctt aactggaaaa tatattggct acaacaatac    360
tacggtagca caatcacctt atggtgacca ttggcgcaat cttcgacgaa tattatcaat    420
tgaaatactc tcatctcatc gtttaaattc cttcttggaa atacgaagag atgagattat    480
```

```
gagactaata caaaagctag cacaaaaatc atacaatggt ttcaccgaag tggaacttag      540
acctatgttt tcggaaatga catttaatac tataatgaga atggtgtcgg ggaaaagata      600
ctatggaaat gattgtgatg tgagtgatgt tgaggaagca aggttgttta gagggataat      660
taaagaggtt gttagtttag gaggagctaa caacgttggt gattttttgg gttttttaag      720
gtggtttgat tttgatggtt tggaaaagag gcttaagaag attagtaaga gaaccgatgc      780
atttttacaa gggcttattg atgaacatcg ttttggaaag aggaatagta acactatgat      840
tgatcatctc ttaacacagc aacaatcaca acccgaatat tatacggacc aaatcatcaa      900
aggacttatg gtggttatgt tacttgcggg aacagacaca tcatccgtaa caatagaatg      960
ggctatgtcc aatttactaa accatccaga ataatgaag aaggcaaaaa atgagttgga     1020
cacccatata ggacatgatc gccaagtaga tgagcatgac atttcaaaac ttccttatct     1080
tcaaagcatt gtctatgaaa cccttcgact acatgcagca gctccattat tagtgcctca     1140
tttgtcatca gaagattttt ccttaggagg atataatatc ccacaaaaca caattttgat     1200
ggtgaatgct tgggtcattc atagagatcc aaatttgtgg agtgatccta cttgttttaa     1260
gccagagagg tttgagaaag aaggtgaggt gaataaatta cttcatttg ggttgggtag     1320 aagggcttgt ccaggagaaa acttatccca aaggactgag ggcttgactt tgggcttatt     1380
gattcagtgt tttgagtgga aacgaatagg tgaagaaaaa attgacatgg ttgaagcaaa     1440
agggatcacg gcgggaaaaa agacttcctt aaatgcaatg tgtaaagtgc gacatccatt     1500
gaagattaac gatgtttttt agttttatt aatgttcgag attcgttgaa acatgcaca     1560 tgatgcaaac atgttga                                                   1577

<210> SEQ ID NO 17
<211> LENGTH: 1668
<212> TYPE: DNA
<213> ORGANISM: Cicer arietinum

<400> SEQUENCE: 17
atggggatcc tttccttgtt gtgctactct ctcttttatc tttctttctt ttcatcatt       60 aggcttttgt tccaatcaag aaaattcaaa aatctcccac caggtccacc ttctcttccc      120
ataattggca acctccatca tctcaaacgt cccctccacc gcacctttaa gggactctct      180
aaaacttatg gtgatatcat ttctctttgg tttggttcac gtcttgttgt tgttgtttct      240
tctctatccg aattccaaca atgcttcact aaaaacgatg ttgtcctagc aaataggcct      300
cgttttctct ctggaaaata catcttctac aattatacta ccttaggatc cacctcttac      360
agtgaacact ggcgcaacct tcgtcgtatc acttccctcg atgttctttc gaaccaccgc      420
atcaacaact tctctggagt ccgaagggat gagactcaac gattaatcac gaagttggcc      480
gaggattcat ccacttcctt tgctgaagta gaacttagtt tcagattcta cgatatgacc      540
ttcaacaaca tcatgcgaat gatccctgga aagagatact acggagaaga ttgtgacatg      600
agtgatcttc aagaagcaag tcaattcagg gatatggtta ctgaactgct gcaattgtct      660
ggtgcaaata acaaaactga tttcatgcct ttgcttaaat ttttgattt tgaaaacttg      720 gagaaaaggg ttaagaatat tgctgacaaa acggacgcat tcttgagagg cctccttcaa      780
gaacaacgca acaagaagga acgtacaaac accatgattg accatcttct aaatttgcaa      840
gaatcacaac ctgagtacta cactgatcag atcatcaaag gccttgcttt ggccatgctc      900
cttgctggaa ccgactcatc tgctgtaact ttagagtggg caatgtctaa tttgttgaac      960
catccagaga tattgaagaa ggtaaaggat gaattggata ttcatgtagg acaagatcgt     1020
```

```
ttggtagatg aatcagacct tccaaaactt acttatctta aaaatgtcat ctatgagacg    1080
cttcggttgt gtactcccgc tcctttgtta ttaccacact caacttcaga tgattgcatt    1140
attggaggat ataaagtacc acgagacacc atagtattga ttaatgcatg ggccattcac    1200
agagatccta agtcatggag tgaggccaca agcttcaagc cggagaggtt tgacaaaaaa    1260
ggggagattg aaaaggtgat tgcatttggg atgggaagaa gagtgtgtcc tggagaagct    1320
ttggctcttc gaacaattag catgactttg gcattattgg ttcaatgctt tgattggaaa    1380
cgtacaagtg atgacaagat tgatatggca gaacgagatg gattcgtttt aacaaaattg    1440
attccattaa aggccatgtg taaaactcgt ccggtggtca acaaggtttt caagtaatta    1500
acttatatcg caattggttg atagtccgat gctatattat tcatattaat tatttcatttt    1560 gtaattttgt ggaatccaga gagaaagtac cgtgctttct caaataagtg tagcgaatat    1620
gcaaataaag taccgtatct ggattttctc taaaaaaaaa aaaaaaaa                1668
```

<210> SEQ ID NO 18
<211> LENGTH: 1781
<212> TYPE: DNA
<213> ORGANISM: Cicer arietinum

<400> SEQUENCE: 18

```
tcggcacgag atttacaagt aacaatatag caagcatttc actaatcaaa acaaacacaa      60
tcattatggg gatcttttcc ttcttcgcat actctctctt ttatctttct atattttttca    120 ttttcaggct tttgttccaa tcaagaaaat tcaaaaatct cccaccaggt ccaccttctc     180
ttcctataat tggcaacttc catcatctca aacgtcccct ccaccgcact ttcaaaggac     240
tttctaaaac atatggtgat atcatttcac tttggtttgg atcacgtctt gtggttgttg     300
tttcttctct atctgaattt caacaatgtt ttacaaaaaa cgatgttgtc ctagctaata     360
ggccacggtt cctctctgga aaatacatct tctacaacta tacgacttta ggatccacat     420
cctacagtga acattggcgc aaccttcgtc gtatcacttc gctcgatgtt ctttcaaacc     480
accgtatcaa caacttctct ggagtccgaa gggatgagac tcaacgacta atcacaaagt     540
tggctgaaga ttcatccact tcctttgctg aagtagaact tagtttcaga ttctatgata     600
tgaccttcaa caacatcatg cgaatgatct ctggaaagag atactacgga gaagattgtg     660
acatgagtga tcttcaagaa gccagtcaat tcagggatat ggttactgaa ctgttgcaat     720
tgtctggtgc aaataacaaa actgattca tgcctttgct taaatttttt gattttgaaa      780
acttggagaa aagggttaag aatattgctg acaaaacgga cgcattcttg agaggactcc     840
ttcaagaaca acgcaacaag aaggaacgta caaacaccat gattgaccat cttctaaatt     900
tgcaagaatc acaacctgag tactacactg atcagatcat caaaggcctt gctttggcta     960
tgctccttgc tggaaccgac tcatctgctg taacttagag tggtcaatg tctaatttgt     1020 tgaaccatcc agaggtattg aagaaggtaa gagatgaatt ggatactcat gtaggacaag    1080
atcgtttggt agatgaatca gaccttccaa aacttactta cctaaaaaat gtcatctatg    1140
aaacgcttcg gttgtgtact cctgctccat tgttattacc acactcaact tcagatgatt    1200
gcattattgg aggatataaa gtaccaagag acaccatagt attgatcaat gcatgggcca    1260
ttcacaggga tcctaagtca tggagtgagg ccacaacctt caagccggag aggtttgaca    1320
aaaaggggga gattgaaaag gtgattgcat ttgggatggg aagaagagtg tgtcctggag    1380
aagctttggc tcttcgtaca attagcatga ctttggcatt attgattcaa tgctttgatt    1440
ggaaacgtac aagtgatgac atgattgata tggcagaacg agatggattc gtcttgacaa    1500
```

```
aattggttcc attaaaagcc atgtgtaaaa ctcgtccggt cgtaaacaaa attttcaagt    1560
agctaatttg tgccgcaact gattgtttat cgatatttt gtatatgtta tgtattcccc     1620
taataattta atcatttatt aattatggaa ggaaagtata ctgcgtgctc aaataagtgt    1680
agtatttgta gtgagtgtgc acaagaaatc cttgtataac tttgtgcaac tggattttct    1740
taaataaaaa gttactgttt attaaaaaaa aaaaaaaaa a                         1781
```

<210> SEQ ID NO 19
<211> LENGTH: 1806
<212> TYPE: DNA
<213> ORGANISM: Glycyrrhiza echinata

<400> SEQUENCE: 19

```
caagaatcaa ccgaacaagc atcaagcaat attaatttaa gtagccaaaa caaaaccacc    60
aacaagccat ggagattcta tccctcttgt cctactccgt cttctatctt gctctatttt    120
tcatattcaa cattgtgatc agagcaagaa aattcaaaaa cctcccaccg ggtccacctt    180
cgcttcccat aatcggaaac ctccaccacc tcaaacgccc cctccaccgc accttcaagg    240
ggttgtcgga aaagtacggc catgtgtttt ccctatggtt tggatcacgc ctcgtcgtcg    300
tggtttcctc tgcatctgaa ttccaacagt gtttcactaa aaacgacgtc gtcctggcaa    360
acaggccccg ctttctctcg ggaaaataca tcttttacaa ctacaccacc ttggggtcca    420
catcctatgg cgagcactgg cgcaacctcc gtcgtatcac cgccctcgac gtcctttcaa    480
accaccgcat caacagcttc tccggaatcc aagggacga gacacaaagg ctcataacga     540
ggcttgccga tgactcgtcc acgaactttg ccgaaatgga actcagctct aggctctatg    600
acatgacgtt caacaacatc atgagaatga tctctgggaa gaggtattat ggggaggact    660
gtgacacgtc agatctccaa gaagcaagcc agttcaggga catggtgtct gagttgctac    720
agttgtctgg ggccaacaac aagactgact tcatgccatt gctcaggttc ctcgactttg    780
aaaacctaga gaagaggctc aaggacatca gtggcaaaac cgatgccttc ttgagaggac    840
tcattgaaga gcaccgcacc aagaaggagc gtgcaaatac catgatagat catctcctca    900
atctccaaga ctcacagcct gagtactata ccgatcaaat catcaaaggc cttgctctgg    960
ccatgctcct gcgggaacc gactcgtctg ctgtaacttt ggagtggtcg atgtccaatt     1020
tgttgaacca tccagaggta ttgaagaagg taaaggatga attggataca catgttggcc    1080
aagatcgctt ggtagatgag tcagaccttc caaaactcac ttaccttaaa aacgttatca    1140
atgagacgct tcggttgtac actccggctc cgttgttact accgcactcg acttcagatg    1200
agtgcaatat tggaggatac aaggttccac aagacaccat agtattgatt aatgcctggg    1260
ccattcacag ggaccctgaa ttgtggactg aagccacgac tttcaagcct gagaggtttg    1320
agaaaaaggg tgagttggaa aagttaattg cctttgggat gggaagaagg gcatgtcccg    1380
gagaaggctt ggctattcgg gcaattagca tgactttggc gttattgatt caatgctttg    1440
attggaagct tataaatggt gataagattg acctggcaga gagggatgga ttcaccttga    1500
caaagttggt tcccctaaag gccatgtgta aatcacgtcc agtcatcaac aaggttttca    1560
agcagtaatt catcacccac tggagtaact agatcaattt tcgaaagata tatatgtatt    1620
cataataatg atatattgat atctgtaatt tttcttggat cctggtagta cacatatgca    1680
caaatactat atgcgtgctc aaataagtgt acaaggatca tctatgtgta attagtatgc    1740
acaaggcgtc atttgtgtag ctttgtgcaa ctggatttaa ttctgaaaaa gttttttgct    1800
ttttat                                                              1806
```

<210> SEQ ID NO 20
<211> LENGTH: 1820
<212> TYPE: DNA
<213> ORGANISM: Glycyrrhiza echinata

<400> SEQUENCE: 20

```
cacatgcaaa ggtgattcag caatagaatc agccgaacaa gcatcaagca atattaattt      60
aagtagccaa aacaaaacca ccaacaagcc atggatattc tatccctctt gtcctactcc     120
gtcttctatc ttgctctatt tttcatattc aacattgtga tcagagcaag aaaattcaaa     180
aacctcccac cgggtccacc ttcgcttccc ataatcggaa acctccacca cctcaaacgc     240
cccctccacc gcaccttcaa ggggttgtcg gaaaagtacg gccatgtgat ttccctatgg     300
tttggatcac gcctcgtggt cgtagtttcc tccgcatctg aattccaaca gtgtttcacc     360
aaaaacgacg tcgtcctggc aaacaggccc cgctttctct cgggaaaata catcttttac     420
aactacacca ccttggggtc cacatcctat ggcgagcact ggcgcaacct ccgtcgtatc     480
accgccctcg acgtcctttc aaaccaccgc atcaacagct tctccggaat ccgaagggac     540
gagacacaga ggctcataac gaggcttgcc gatgactcat ccacgaactt tgccgaaata     600
gaactcagtt acaggttcta tgacatgaca ttcaacaaca tcatgagaat gatctccggg     660
aagaggtact atgggagga ctgtgacatg tcagatcttc aagaagcaag ccagttcagg     720
gacatggtgt ctgagttgtt gcagttgtct ggggccaaca acaagaccga cttcatgcca     780
ttgctcaggt cctcgacttt tgaaaacctg gagaagaggc tcaaggatat cagtggcaaa     840
accgatgcct tcttgagagg actcatccaa gagcaccgcg ccaagaagga acgtgcaaat     900
accatgatag atcatctcct caatctccaa gactcacagc tgagtacta caccgatcaa     960
atcatcaaag gccttgctct ggccatgctc cttgcgggaa ccgactcgtc tgctgtaact    1020
ttggagtggt cgatgtccaa tttgttgaac catccagagg tattgaagaa ggtaaaggat    1080
gaattggata cacatgttgg ccaagatcgc ttggtagatg agtcagacct tccaaaactc    1140
tcttaccttaa aaacgttat caatgagacg cttcggttgt acactccggc tccgttgtta    1200
ctaccgcact cgacttcaga tgagtgcaat attggaggat acaaggttcc acaagacacg    1260
atagtattga ttaatgcctg ggccattcac agggaccctg aattgtggac tgaagccacg    1320
actttcaagc ctgagaggtt tgagaaaaag ggtgagttgg aaaagttaat tgccctttggg    1380
atgggaagaa gggcatgtcc cggagaaggc ttggctattc gggcaattag catgacttg    1440
gcgttattga ttcaatgctt tgattggaag cttacaaatg gtgataagat tgacatggca    1500
gagagggatg gattcacctt gacaaaattg gttcccctaa aggccatgtg taaatcacgt    1560
ccagtcatca acaaggtttt caagcagtaa ttcatcatcc actcgagaag atcagttttc    1620
gaaagatatg tgtattcata ataatgatat atttgtaatt tttctagtat ccaggtagta    1680
cgcgtgcatt tgcacaaata ccatgtgtgc tcaaagaagt gtacaagggt catctatgtg    1740
tacttagtat gcacaaggcg ttttttgttgt ataactttgt gtaactggat ttgctcatat    1800
aaaaagttag ttgctttcac                                                1820
```

<210> SEQ ID NO 21
<211> LENGTH: 1500
<212> TYPE: DNA
<213> ORGANISM: Lotus corniculatus var japonicus

<400> SEQUENCE: 21

```
atggatatca tctccttcct ttactattct ctcttctacg tagctttgtt tgccataatc      60
```

-continued

```
aaactcttcc tcggctcaag aaagttcaaa aacctccctc ccggtccaac ctcacttccc    120
ataattggca accttcacca cctcaaacgc cccctccacc gcaccttcag ggcgctgtct    180
gagaagtatg gcgacgtctt ctccctatgg ttcggaaacc gtcttgtggt ggtggtctcc    240
tccttcgccg atgtccagga atgcttcacc aaaaacgacg tggtgcttgc gaaccggcca    300
cgcttcctct ctggaaagta catcttctac aactacacca ccttaggttc cacctcctac    360
ggtgagcact ggcgtaacct ccgccgcatc acctccttgg atgtcctctc caaccaccgc    420
atcaacagct tctccccgat ccgccgcgat gaaaccacac ggctgattag gaagctggct    480
gaggactctg ctaagaactt ctccgaagtg gagctcacct caaggttctt cgacatgacc    540
ttcaacaaca tcatgaggat gatctccggg aagaggtact atggagagga ttgtgacatg    600
accgagcttc aggaggcgag cgagttcagg gacatggtga ccgagttgct gcagttgtcc    660
ggggcgaata acaaggccga tttcatgcct attctcaggc ttgttgattt tgaagggttg    720
gagaagaggg tgaaagggat tagttccaaa actgataggt tcttgagagg actccttcaa    780
gagcaccgtg acaagaagca gcgtacagca ataccatga ttgatcatct cctaactctg    840
caagagtcac agcctgaata ctatactgat caaatcatca aaggccttgc tttggccatg    900
cttcttgctg gaaccgattc atcagctgtc accttagaat ggtcaatgtg caacgtactt    960
aactatccag aggtattgga gaagataaag gctgagttgg acactcatgt tggccaagac   1020
cgcttggtag atgagtcaga cattccaaaa ctcacttacc ttaaaaatgt tatcaatgag   1080
acacttcggc tatacacccc agcaccgctc ctattaccac actccgcttc agatgattgc   1140
actattggtg gctacaaagt cccacgtgac acaatagtgt tgattaatgc ttgggcgcctt   1200 catagggacc cacaattgtg gactgaagcc acaactttca agccagagag gtttgataag   1260
aagggagagt tggagaagtt gattccattt gggttaggaa gaagggcgtg ccccggagag   1320
ctcttggcga ttcgtgcaat cagcatgact ctagcgttgt tgattcagtg ctttgattgg   1380
aaacgtgtga gtgatgaaga gattgatatg ggcgagcgag atgggtttgt cttgatgaag   1440
tctattcctg tgaaggctat gtgtaaatca cgcccagtca taaacaatgt tttcaagtag   1500
```

PLANT ISOFLAVONOID HYDROXYLASES AND METHODS OF USE THEREOF

This application is a division of U.S. application Ser. No. 10/976,190, now U.S. Pat. No. 7,442,851, filed Oct. 28, 2004 which claims the priority of U.S. Provisional Patent Appl. Ser. No. 60/515,559 filed Oct. 29, 2003, the entire disclosures of which are specifically incorporated herein by reference.

BACKGROUND OF THE INVENTION

1. Field of the Invention

The present invention relates generally to the field of molecular biology. More specifically, the invention relates to plant isoflavonoid hydroxylase genes and methods of use thereof.

2. Description of the Related Art

Isoflavonoids are a subclass of phenylpropanoid metabolites distributed primarily in legumes (Dixon and Sumner, 2003). They possess a wide range of biological activities (Dixon, 1999), but most research has focused on their functions as pathogen-inducible antimicrobial compounds (phytoalexins) (Ingham, 1982; Dewick, 1993; Dixon, 1999) or as dietary phytoestrogens implicated in human disease prevention (Adlercreutz and Mazur, 1997; Dixon and Ferreira, 2002). Different legume species produce different classes of isoflavonoid phytoalexins, of which substituted pterocarpans, such as medicarpin from alfalfa and pisatin from pea, are the best known.

Complex isoflavonoid derivatives such as the rotenoids rotenone, deguelin, and amorphigenin from *Amorpha, Lonchocarpus, Derris,* and *Tephrosia* species possess insecticidal and parasiticidal properties (Lambert et al., 1993; Nicholas et al., 1985). Maackiain, which accumulates along with medicarpin (the major phytoalexin in *Medicago* species) in red clover (*Trifolium pratense*), subterranean clover (*T. subterraneum*), and chickpea (*Cicer arietinum*) (Dewick and Ward, 1978; Higgins, 1972; Ingham, 1982), has recently been shown to have larvicidal activity against caterpillars of *Heliocoverpa armigera* that attack chickpea (Simmonds and Stevenson, 2001).

The biosynthesis of complex isoflavonoids such as the antimicrobial pterocarpans requires hydroxylation of the isoflavonoid nucleus at either the 2' and/or 3' positions. Isoflavone 2'-hydroxylase (I2'H) activity has been identified in microsomal fractions of elicited cells of soybean (Kochs and Grisebach, 1986), chickpea (Clemens et al., 1993; Gunia et al., 1991; Hinderer et al., 1987) and alfalfa (*Medicago sativa*) (Choudhary et al., 1990), and an I2'H(CYP81E1) gene characterized from licorice (*Glycyrrhiza echinata* L.). Recombinant CYP81E1 catalyzed the 2'-hydroxylation of formononetin (7-hydroxy, 4'-methoxyisoflavone) and the 2'- and 3'-hydroxylation of daidzein (7,4'-dihydroxyisoflavone) in vitro in yeast microsomes (Akashi et al., 1998). Several cDNA clones with high sequence identity to I2'H have been isolated from elicited *Lotus japonicus* and chickpea cell suspension cultures by PCR strategies based on P450 conserved motifs (Overkamp et al., 2000; Shimada et al., 2000). However, functional characterization has not been reported.

Hydroxylation at the 3'-position of the B-ring of an isoflavone is a key step in the formation of the methylenedioxy bridge of maackiain (Clemens and Barz, 1996; Clemens et al., 1993; Dewick and Ward, 1978), and in the formation of rotenoids (Dixon, 1999). Isoflavone 3'-hydroxylase (I3'H) activities have been detected in the fungus *Fusarium* (Mackenbrock and Barz, 1983); in roots, leaves and elicited cell suspension cultures of chickpea (Clemens et al., 1993; Hinderer et al., 1987); and more recently in human liver (Tolleson et al., 2002) in which P450 enzymes are presumably involved in isoflavone catabolism.

While the foregoing studies have provided a further understanding of the metabolism of plant secondary metabolism, genes encoding I3'H have not yet been identified. Further, functional characterization of genes encoding I2'H has not been carried out in plants. The identification and characterization of such genes encoding isoflavone hydroxylases would allow the creation of novel plants with improved phenotypes and methods for use thereof. There is, therefore, a great need in the art for the identification of plant isoflavonoid hydroxylase genes.

SUMMARY OF THE INVENTION

In one aspect, the invention provides an isolated nucleic acid sequence encoding a plant isoflavone 3'-hydroxylase. In certain embodiments, the nucleic acid sequence may be further defined as selected from the group consisting of: (a) a nucleic acid sequence encoding the polypeptide of SEQ ID NO:6; (b) a nucleic acid sequence comprising the sequence of SEQ ID NO:5; (c) a nucleic acid sequence hybridizing to SEQ ID NO:5 under conditions of 0.15 M NaCl and 70° C.; (d) a nucleic acid sequence comprising at least 85% sequence identity, including at least 90%, 95% and 98% identity, over the full length the nucleic acid sequence of SEQ ID NO:5; and (e) a nucleic acid sequence complementary to the nucleic acid sequence of polynucleotide sequence of (a), (b), (c) or (d).

In another aspect, the invention provides an isolated nucleic acid sequence encoding a plant isoflavone 2'-hydroxylase. In certain embodiments, the nucleic acid sequence may be further defined as selected from the group consisting of: (a) a nucleic acid sequence encoding the polypeptide of SEQ ID NO:2; (b) a nucleic acid sequence comprising the sequence of SEQ ID NO: 1; (c) a nucleic acid sequence hybridizing to SEQ ID NO: 1 under conditions of 0.15 M NaCl and 70° C.; (d) a nucleic acid sequence comprising at least 85% sequence identity, including at least 90%, 95% and 98% identity, over the full length the nucleic acid sequence of SEQ ID NO: 1; and (e) a nucleic acid sequence complementary to the nucleic acid sequence of polynucleotide sequence of (a), (b), (c) or (d).

In yet another aspect, the invention provides a recombinant vector comprising an isolated polynucleotide of the invention. The nucleic acid sequence may be in sense orientation and may be an antisense oligonucleotide of a coding sequence provided by the invention. Such an antisense oligonucleotide may, but need not necessarily comprise the full length of a coding sequence provided by the invention. In certain embodiments, the recombinant vector may further comprise at least one additional sequence chosen from the group consisting of: a regulatory sequence, a selectable marker, a leader sequence and a terminator. In further embodiments, the additional sequence is a heterologous sequence and the promoter may be constitutive, developmentally-regulated, organelle-specific, inducible, inducible, tissue-specific, constitutive, cell-specific, seed specific, or germination-specific promoter. The recombinant vector may or may not be an isolated expression cassette.

In still yet another aspect, the invention provides an isolated polypeptide comprising the amino acid sequence of SEQ ID NO:2, or a fragment thereof having isoflavonoid hydroxylase activity, and including sequences with at least 85% sequence identity, including at least 90%, 95% and 98% identity, to this sequence. The invention also provides an isolated polypeptide comprising the amino acid sequence of SEQ ID NO:4 or SEQ ID NO:6, or a fragment thereof having isoflavonoid hydroxylase activity, and including sequences with at least 85% sequence identity, including at least 90%, 95% and 98% identity, to this sequence. As used herein, the term "isoflavonoid hydroxylase activity" refers to the ability to catalyze at least one step in the isoflavonoid biosynthetic pathway.

In still yet another aspect, the invention provides a transgenic plant transformed with a selected DNA comprising a nucleic acid sequence of the invention encoding plant isoflavone 3'-hydroxylase and/or 2'-hydroxylase activity. The transgenic plant may be a monocotyledonous or dicotyledonous plant and may be a legume. The plant may also be an $R_0$ transgenic plant and/or a progeny plant of any generation of an $R_0$ transgenic plant, wherein the transgenic plant has inherited the selected DNA from the $R_0$ transgenic plant.

In still yet another aspect the invention provides additional plant isoflavonoid hydroxylase coding sequences. In one embodiment of the invention, such sequences may be further defined as selected from the group consisting of: (a) a nucleic acid sequence encoding the polypeptide encoded by any of SEQ ID NOs:15-21; (b) a nucleic acid sequence comprising the sequence of any of SEQ ID NOs:15-21; (c) a nucleic acid sequence hybridizing to any of SEQ ID NOs:15-21 under conditions of 0.15 M NaCl and 70° C. and; (d) a nucleic acid sequence comprising at least 85% sequence identity over the full length the nucleic acid sequence of any of SEQ ID NOs: 15-21; and (e) a nucleic acid sequence complementary to the nucleic acid sequence of polynucleotide sequence of (a), (b), (c) or (d). As used herein, "any of SEQ ID NOs:15-21" specifically includes each of SEQ ID NO:15, SEQ ID NO:16, SEQ ID NO:17, SEQ ID NO:18, SEQ ID NO:19, SEQ ID NO:20 and SEQ ID NO:21, both individually and in all possible combinations thereof.

In still yet another aspect, the invention provides a seed of a transgenic plant of the invention, wherein the seed comprises the selected DNA. The invention also provides a host cell transformed with such a selected DNA. The host cell may express a protein encoded by the selected DNA. The cell may have inherited the selected DNA from a progenitor of the cell and may have been transformed with the selected DNA. The cell may be a plant cell.

In still yet another aspect, the invention provides a method of increasing the pest and/or disease resistance of a plant comprising introducing into the plant a nucleic acid encoding isoflavone 3'-hydroxylase and/or 2'-hydroxylase. In a method of the invention, up-regulating isoflavone 3'-hydroxylase and/or 2'-hydroxylase may be carried out by introducing a recombinant vector of the invention into a plant. Down-regulating may also be carried out, including by use of antisense oligonucleotides provided by the invention. The vector may be introduced by plant breeding and/or direct genetic transformation.

In still yet another aspect, the invention provides a method of making food for human or animal consumption comprising: (a) obtaining the plant of the invention; (b) growing the plant under plant growth conditions to produce plant tissue from the plant; and (c) preparing food for human or animal consumption from the plant tissue. In the method, preparing food may comprise harvesting plant tissue. In certain embodiments, the food is starch, protein, meal, flour or grain.

In still yet another aspect, the invention provides a method of producing a nutraceutical composition comprising (a) obtaining a plant in accordance with the invention; (b) growing said plant under plant growth conditions to produce plant tissue from the plant; and (c) preparing a nutraceutical composition for human or animal consumption from said plant tissue.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein.

C, 2'-hydroxyformononetin (2'HF) standard. The UV spectrum and retention time of the 2'HF peak in (B) exactly matched those of the authentic standard.

Figure 6:
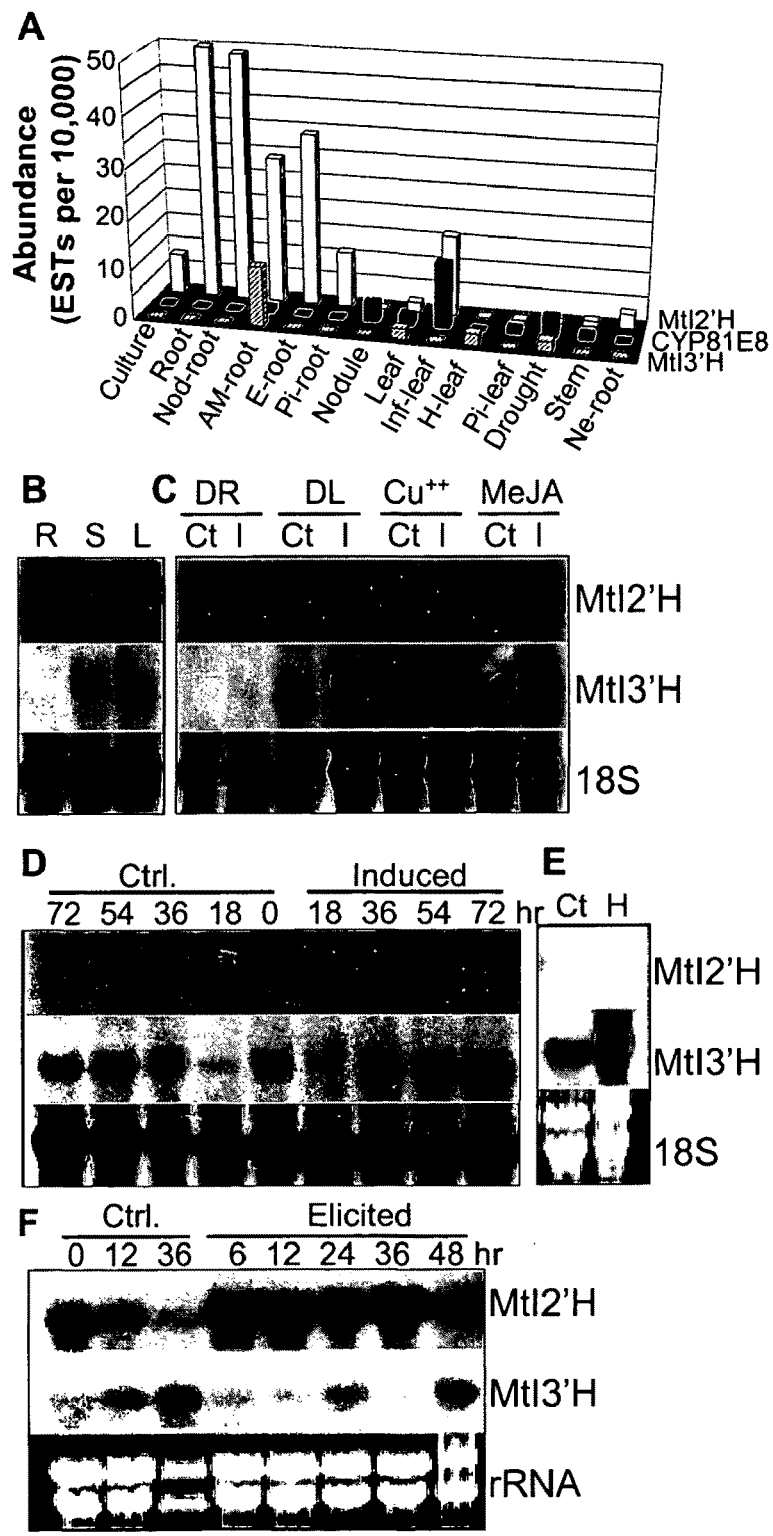

FIG. 6. Analysis of tissue- and biotic/abiotic stimulus-specific expression of MtI2'H (CYP81E7)(SEQ ID NO:1), CYP81E8 (SEQ ID NO:3)and MtI3'H (CYP81E9) (SEQ ID NO:5) transcripts in *M. truncatula*. (A) In silico analysis of EST abundance in a number of different cDNA libraries, analyzed from data in the TIGR *M. truncatula* gene index. Libraries (with total EST counts in parentheses) are: yeast elicitor induced cell suspension cultures (Culture; 8526); non-nodulated roots (Root; 5519); nodulated roots (Nodroot; 8697); *Glomus versiforme* and *Glomus intraradices* (arbuscular mycorrhizal fungus) infected roots (AM-root; 15916); fungal elicitor-treated root (E-root; 4967); phosphate-starved root (Pi-root; 5532); root nodule (Nodule; 14231); leaf (7425); *Phoma medicaginis* infected leaf (Inf-leaf; 3116); beet armyworm caterpillar damaged leaves (H-leaf; 9662); phosphate starved leaf (Pi-leaf; 8301); drought stressed seedlings (Drought; 7505); stem (9943); nematode infected root (Ne-root; 3154). (B-F) RNA gel blot analysis of MtI2'H (CYP81E7) and MtI3'H (CYP81E9) transcripts. (B) Tissue-specific expression in roots (R), stems (S) and leaves (L) of mature plants at the same developmental stage. (C). Effects of drought on root (DR) and leaf (DL) tissue, and of elicitation with copper chloride (Cu++) and methyl jasmonate (MeJA) on leaf tissue. Ct, parallel control treatment; I, induced treatment. (D) Time course for effects of inoculation of leaf material with *Phoma medicaginis* (Induced) and parallel control treatments (Ctrl). (E) Effects of insect herbivory with overnight feeding by beet armyworm caterpillars, (H) compared to a parallel control (Ct). (F) Time course for exposure of cell suspension cultures to yeast elicitor (Elicited) with parallel water-treated controls (Ctrl.).

DETAILED DESCRIPTION OF THE INVENTION

The invention overcomes the limitations of the prior art by providing plant isoflavonoid hydroxylase coding sequences. Two sequences were identified and functionally characterized by expression in yeast. The recombinant enzymes in yeast microsomes utilized the same isoflavone substrates, but produced different products hydroxylated at the 2' and/or 3' positions of the B-ring. When transiently expressed in alfalfa leaves, green fluorescent protein fusions of the isoflavone 2'- and 3'-hydroxylases localized to the endoplasmic reticulum. The isoflavone 2'-hydroxylase was functional when expressed in vivo in *Arabidopsis*. Differential tissue-specific and biotic/abiotic stress-dependent expression patterns were observed for the isoflavone 2'-hydroxylase and 3'-hydroxylase genes, indicating differential involvement of 2'- and 3'-hydroxylated isoflavonoids in pathogen defense and insect-induced responses, respectively, in *Medicago*. The alteration of isoflavone biosynthesis by these sequences also has nutritional significance given the dietary importance of this class of biomolecules.

This is the first report of the isolation of a coding sequence for isoflavone 3'-hydroxylase (I3'H). The invention therefore represents an important advance in that it allows manipulation of new steps in the isoflavonoid biosynthetic pathway. The invention allows selection of the isoflavonoid makeup of an organism, for example, a plant. This may be used, for example, to increase resistance to pests, including herbivory by insects and animals, and/or increase disease resistance.

Nutritional and/or food quality benefits may also be obtained by altering and/or increasing isoflavonoid biosynthesis. This may be carried out to achieve the many health benefits known to be associated with isoflavones. It may therefore be beneficial to prepare nutraceuticals from the plants provided by the invention. For example, the small shrublet *Eriosema kraussianum* from Southern Africa has been used by the Zulus for curing impotency. It contains di-prenylated isoflavones (kraussianones) that have been shown to possess similar activity to Viagra in an in vitro test with rabbit penile muscle (Drewes et al., 2002). Based on its structure, the biosynthesis of kraussianone can be proposed to occur via genistein, 2'-hydroxygenistein, prenyl transfer to the 6 and 5'-positions of 2'-hydroxygenistein, and final cyclization of the two prenyl groups to give dimethlychromene rings. Genistein can be introduced into plants by genetic transformation with isoflavone synthase (IFS) (Liu et al., 2002). This could be converted to 2'-hydroxygenistein using the isoflavone 2'-hydroxylase compositions described herein.

The three sequences that were identified were assigned as CYP81E subfamily members, designated CYP81E7, CYP818 and CYP819. Two of the three sequences were functionally characterized by expression in yeast. The sequences share similarity at the amino acid level and utilize the same methylated isoflavone substrates, but encode distinct isoflavone 2'-(CYP81E7) and 3'-(CYP81E9) hydroxylases. The I2'H (CYP81E7) was shown functional in *Arabidopsis*. The differential expression patterns of the I2'H and I3'H genes in response to a variety of biotic and abiotic stimuli was demonstrated.

I2'H occupies a critical position in isoflavonoid biosynthesis in that the 2'-hydroxylation of the B-ring is essential for subsequent reduction by isoflavone reductase to yield an isoflavanone, an obligatory intermediate in the formation of pterocarpan phytoalexins such as medicarpin (Dixon, 1999). It has been suggested that I2'H is the rate determining step in elicitor-induced pterocarpan phytoalexin biosynthesis in chickpea (Hinderer et al., 1987).

Figure 1:
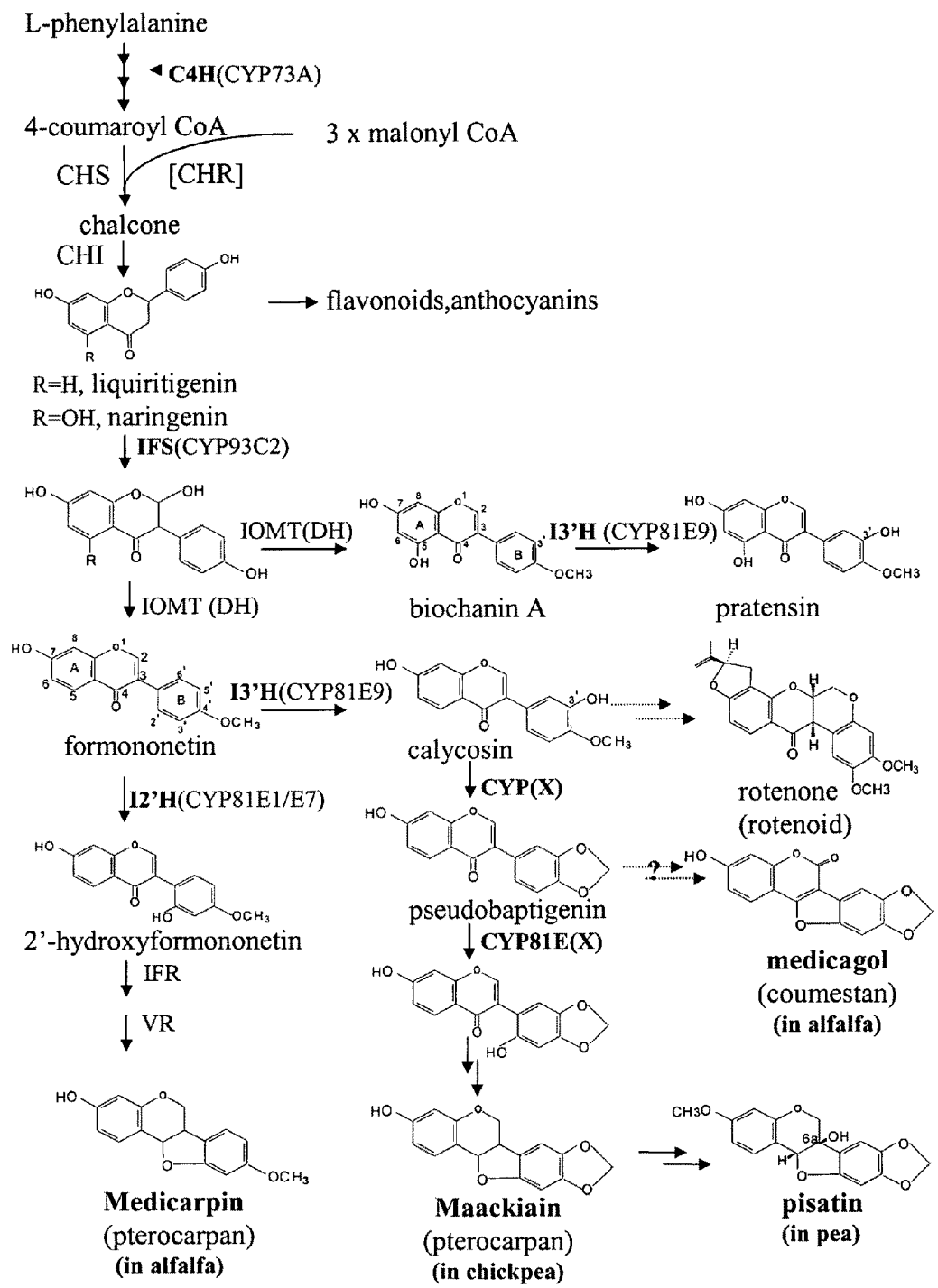
FIG. 1. Biosynthetic pathways leading to complex isoflavonoids in legumes. The compounds shown are found in species as indicated. The enzymes are: CYP73A, cinnamate 4-hydroxylase; CHS, chalcone synthase; CHR, chalcone reductase; CHI, chalcone isomerase; CYP93C,2-hydroxyisoflavanone synthase (also known as isoflavone synthase, IFS); IOMT, 2-hydroxyisoflavanone 4'-O-methyltransfrease; DH, 2-hydroxyisoflavanone dehydratase; CYP81E1/7, isoflavone 2'-hydroxylase (I2'H); CYP81E9, isoflavone 3'-hydroxylase (I3'H); IFR, isoflavone reductase; VR, vestitone reductase, CYPX, P450 catalyzing methylenedioxy ring closure. CYP81E(X), P450 catalyzing 2'-hydroxylation of pseudobaptigenin. Dotted arrows indicate pathways that are yet to be fully confirmed. Double arrows indicate two or more reactions. The numbering system for isoflavones is shown for formononetin and biochanin A. Note that the 2' and 5', and 3' and 6', positions are synonymous due to rotation about the bond linking the aryl group to the 3-position of the heterocyclic ring.

The biosynthesis of isoflavonoids diverges from the ubiquitous flavonoid pathway as shown in FIG. 1, which also provides details of the A and B-ring and position designations of isoflavonoid compounds. The 5-deoxyflavanone liquiritigenin is converted to an isoflavone and then undergoes several steps of hydroxylation, methylation, reduction and ring closure to form pterocarpans such as medicarpin and maackiaian (Dewick and Martin, 1979; Dixon, 1999). The 5-hydroxyflavanone naringenin is also a starting point for synthesis of isoflavonoids such as biochanin A and pratensin in chickpea and red clover (Clemens et al., 1993; Dewick and Ward, 1978) (FIG. 1). Hydroxylations catalyzed by membrane-bound, NADPH-dependent cytochrome P450 monooxygenases are critical steps in the biosynthesis of complex isoflavonoids. For example, 2-position hydroxylation of liquiritigenin and naringenin accompanied by B-ring migration from the 2 to the 3-position occurs at the entry point into the isoflavonoid pathway (Kochs and Grisebach, 1986), whereas 2'- or 3'-position hydroxylation of the B-ring of isoflavones is essential for formation of pterocarpans and/or methylenedioxy substituted compounds such as maackiain and pisatin (Dewick and Ward, 1978; Clemens et al., 1993; Gunia et al., 1991; Hinderer et al., 1987) (FIG. 1). 6a-Hydroxylation of pterocarpans occurs in the biosynthesis of the glyceollins in soybean (Kochs and Grisebach, 1989) and of pisatin in pea (FIG. 1).

I2'H is clearly involved in the biosynthesis of the phytoalexin medicarpin in *M. truncatula* roots, elicited cell cultures and infected leaves, where the presence of transcripts correlates with appearance of medicarpin. However, the function of I3'H has been less clear. 3'-Hydroxylation of the B-ring of flavonoids is usually associated with the formation of a methylenedioxy bridge linking positions 3' and 4', as found in maackiain and pisatin (FIG. 1); the proposed pathway involves successive methylation of the 4'-hydroxyl, followed by 3'-hydroxylation and closing of the ring by the action of a cytochrome P450 enzyme (CYP(X) in FIG. 1) (Dixon, 1999). These reactions are believed to occur prior to 2'-hydroxylation during the biosynthesis of maackiain via pseudobaptigenin in chickpea (Clemens and Barz, 1996; Clemens et al., 1993) (FIG. 1).

M. truncatula I3'H hydroxylates both biochanin A (preferred) and formononetin. In chickpea, the 3'-hydroxylated product of biochanin A, pratensein (FIG. 1), is a naturally occurring constituent (Wong, 1975). However, pratensein has not been reported in either alfalfa or M. truncatula (ILDIS, 1994). 3'-Hydroxylation of biochanin A in chickpea microsomes was suggested to be catalyzed by an enzyme distinct from that responsible for 3'-hydroxylation of formononetin (Clemens et al., 1993), unlike the situation now shown with the recombinant enzymes from Medicago.

P450-mediated 2'-hydroxylation of pseudobaptigenin occurs after 3'-hydroxylation and methylenedioxy bridge formation in maackiain biosynthesis in pea and chickpea (FIG. 1). Pseudobaptigenin is an excellent substrate for M. truncatula I2'H in vitro. However, there is as yet no evidence for formation of maackiain in Medicago species (ILDIS, 1994), as confirmed herein. The detection limit for authentic maackiain by HPLC was 3.5 nmol/g fresh weight; much less than the observed amount of maackiain accumulating in elicited chickpea cell cultures (600 nmol/g fresh weight) (Mackenbrock et al., 1993) or elicited red clover roots (~500 nmol/g fresh weight) (Tebayashi et al., 2001). The only B-ring methylenedioxy-substituted isoflavonoid derivative reported to date from Medicago species is the coumestan medicagol (FIG. 1) (Olah and Sherwood, 1971; ILDIS, 1994). Further study should elucidate the coumestan metabolites made in M. truncatula and the conditions under which they are formed.

The biosynthetic role of I3'H in M. truncatula appears to involve pathways that are independent from those involving I2'H. For example, I3'H is induced in leaves treated with methyl jasmonate or damaged by insect herbivory, conditions under which I2'H is not induced. In contrast, I2'H, but not I3'H, is induced in yeast elicited cell cultures that accumulate medicarpin, and is more strongly induced than the 3'-hydroxylase in Phoma-infected leaves that also accumulate medicarpin (He and Dixon, 2000). The expression pattern indicates involvement of isoflavonoids in insect-mediated responses in M. truncatula. Significantly, the biosynthesis of pterocarpans such as maackiain, and the rotenoids, involves 3'-hydroxylation, and these compounds have anti-insect activity (Bhandari et al., 1992; Dixon, 1999; Nicholas et al., 1985; Simmonds and Stevenson, 2001).

As shown herein, I2'H from M. truncatula can be expressed as a functional protein in Arabidopsis, and therefore may be used to introduce the complete pathway for formation of pterocarpans into plant species that do not possess this pathway. Furthermore, in plants in which I2'H catalyzes an important rate limiting step for pterocarpan biosynthesis, such as legume species, over-expression of I2'H in plants such as alfalfa, pea and soybean may be used to improve disease resistance. (Gunia et al., 1991)

I. Plant Transformation Constructs, Nucleic Acids And Polypeptides

Certain embodiments of the current invention concern plant transformation constructs. For example, one aspect of the current invention is a plant transformation vector comprising one or more isoflavone hydroxylase coding sequence. An exemplary coding sequence for use with the invention encodes the polypeptide of SEQ ID NO:2, SEQ ID NO:4, SEQ ID NO:6 or a polypeptide encoded by any of SEQ ID NOs: 15-21. In certain embodiments of the invention, transformation constructs comprise the nucleic acid sequence of SEQ ID NO:1, SEQ ID NO:3, SEQ ID NO:5 and/or any of SEQ ID NOs:15-21.

Coding sequences may be provided operably linked to a heterologous promoter, in either sense or antisense orientation. Expression constructs are also provided comprising these sequences, including antisense oligonucleotides thereof, as are plants and plant cells transformed with the sequences. The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

Provided herein are also transformation vectors comprising nucleic acids capable of hybridizing to the nucleic acid sequences, for example, of SEQ ID NO:1, SEQ ID NO:3, SEQ ID NO:5 and/or any of SEQ ID NOs:15-21. As used herein, "hybridization," "hybridizes" or "capable of hybridizing" is understood to mean the forming of a double or triple stranded molecule or a molecule with partial double or triple stranded nature. Such hybridization may take place under relatively high stringency conditions, including low salt and/or high temperature conditions, such as provided by a wash in about 0.02 M to about 0.15 M NaCl at temperatures of about 50° C. to about 70° C. for 10 min. In one embodiment of the invention, the conditions are 0.15 M NaCl and 70° C. Stringent conditions tolerate little mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

The invention provides a polynucleotide sequence identical over its entire length to each coding sequence set forth in the Sequence Listing. The invention also provides the coding sequence for the mature polypeptide or a fragment thereof, as well as the coding sequence for the mature polypeptide or a fragment thereof in a reading frame with other coding sequences, such as those encoding a leader or secretory sequence, a pre-, pro-, or prepro-protein sequence. The polynucleotide can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

Another aspect of the present invention relates to the polypeptide sequences set forth in the Sequence Listing, as well as polypeptides and fragments thereof, particularly those polypeptides which exhibit isoflavone 2'-hydroxylase and 3'-hydroxylase activity and also those polypeptides which have at least 85%, more preferably at least 90% identity, and most preferably at least 95% identity to a polypeptide sequence selected from the group of sequences set forth in the Sequence Listing, and also include portions of such polypeptides, wherein such portion of the polypeptide preferably includes at least 30 amino acids and more preferably includes at least 50 amino acids.

"Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" can be readily calculated by known methods including, but not limited to, those described in Computational Molecular Biology, Lesk, A. M., ed., Oxford University Press, New York (1988); Biocomputing: Informatics and Genome Projects, Smith, D. W., ed., Academic Press, New York, 1993; Computer Analysis of Sequence Data, Part I, Griffin, A. M. and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., Stockton Press, New York (1991); and Carillo, H., and Lipman, D., SIAM J Applied Math, 48:1073 (1988).

Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., Nucleic Acids Research 12(1):387 (1984); suite of five BLAST programs, three designed for nucleotide sequences queries (BLASTN, BLASTX, and TBLASTX) and two designed for protein sequence queries (BLASTP and TBLASTN) (Coulson, Trends in Biotechnology, 12: 76-80 (1994); Birren, et al., Genome Analysis, 1: 543-559 (1997)). The BLAST X program is publicly available from NCBI and other sources (BLAST Manual, Altschul, S., et al., NCBI NLM NIH, Bethesda, Md. 20894; Altschul, S., et al., J. Mol. Biol., 215: 403-410 (1990)). The well known Smith Waterman algorithm can also be used to determine identity.

Parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA 89:10915-10919 (1992); Gap Penalty: 12; and Gap Length Penalty: 4. A program which can be used with these parameters is publicly available as the "gap" program from Genetics Computer Group, Madison Wis. The above parameters along with no penalty for end gap may serve as default parameters for peptide comparisons.

Parameters for polynucleotide sequence comparison include the following: Algorithm: Needleman and Wunsch, J. Mol. Biol. 48:443-453 (1970); Comparison matrix: matches=+10; mismatches=0; Gap Penalty: 50; and Gap Length Penalty: 3. A program which can be used with these parameters is publicly available as the "gap" program from Genetics Computer Group, Madison Wis. The above parameters may serve as the default parameters for nucleic acid comparisons.

One beneficial use of the sequences provided by the invention will be in the alteration of plant phenotypes by genetic transformation with isoflavone hydroxylase coding sequences. The isoflavone hydroxylase coding sequence may be provided with other sequences and may be in sense or antisense orientation with respect to a promoter sequence. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

The choice of any additional elements used in conjunction with an isoflavone hydroxylase coding sequences will often depend on the purpose of the transformation. One of the major purposes of transformation of crop plants is to add commercially desirable, agronomically important traits to the plant, as described above.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant, such as all of the coding sequences for isoflavonoid biosynthesis.

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

A. Regulatory Elements

Exemplary promoters for expression of a nucleic acid sequence include plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. In one embodiment of the invention, the native promoter of a isoflavone hydroxylase coding sequence is used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is envisioned that isoflavone hydroxylase coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. In one embodiment of the invention, the native terminator of a isoflavone hydroxylase coding sequence is used. Alternatively, a heterologous 3' end may enhance the expression of sense or anti-sense isoflavone hydroxylase coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xy/E gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228).

Another screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates, or even for whole plant screening. The gene which encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

II. Antisense and RNai Constructs

Antisense and RNAi treatments represent one way of altering isoflavone hydroxylase activity in accordance with the invention. In particular, constructs comprising a isoflavone hydroxylase coding sequence, including fragments thereof, in sense and/or antisense orientation, may be used to decrease or effectively eliminate the expression of an isoflavone hydroxylase in a plant. Alternatively, RNAi and antisense technology may be used to divert substrates to a selected pathway in the biosynthesis of complex isoflavonoids. For example, use of RNAi or antisense I3'H would divert substrates to I2'H and the synthesis of products downstream of I2'H. The converse strategy could also be used. In this manner, the composition of complex isoflavonoids in a plant may be selectively manipulated and beneficial phenotypes obtained.

Techniques for RNAi are well known in the art and are described in, for example, Lehner et al., (2004) and Downward (2004). The technique is based on the fact that double stranded RNA is capable of directing the degradation of messenger RNA with sequence complementary to one or the other strand (Fire et al., 1998). Therefore, by expression of a particular coding sequence in sense and antisense orientation, either as a fragment or longer portion of the corresponding coding sequence, the expression of that coding sequence can be down-regulated.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host plant or part thereof. In certain embodiments of the invention, such an RNAi or antisense oligonucleotide may comprise any unique portion of a nucleic acid sequence provided herein. In further embodiments of the invention, such a sequence comprises nucleic acids complementary to at least 18, 30, 50, 75 or 100 or more contiguous base pairs of the nucleic acid sequence of SEQ ID NO:1, SEQ ID NO:3, SEQ ID NO:5 and/or any of SEQ ID NOs:15-21, including the full length thereof.

Constructs may be designed that are complementary to all or part of the promoter and other control regions, exons, introns or even exon-intron boundaries of a gene. It is contemplated that the most effective constructs will include regions complementary to intron/exon splice junctions. Thus, it is proposed that a preferred embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an RNAi or antisense construct which has limited regions of high homology, but also contains a non-homologous region (e.g., ribozyme; see above) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

III. Genetic Transformation

Suitable methods for transformation of plant or other cells for use with the current invention are believed to include virtually any method by which DNA can be introduced into a cell, such as by direct delivery of DNA such as by PEGmediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety), etc. Through the application of techniques such as these, the cells of virtually any plant species may be stably transformed, and these cells developed into transgenic plants.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Thomas et al., 1990) and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

Another method for delivering transforming DNA segments to plant cells in accordance with the invention is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety; (Thompson, 1995) and rice (Nagatani, 1997).

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al. (1975) and MS media (Murashige and Skoog, 1962).

IV. Production And Characterization Of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}$ M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

V. Breeding Plants Of The Invention

In addition to direct transformation of a particular plant genotype with a construct prepared according to the current invention, transgenic plants may be made by crossing a plant having a selected DNA of the invention to a second plant lacking the construct. For example, a selected isoflavone hydroxylase coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VI. Nutraceuticals

Nutraceutical compositions are preparations of natural ingredients that are multi-component systems consisting of preferably synergistic natural products and supplements to promote good health. The plants provided by the invention contain altered and/or increased isoflavonoid content, which has certain health benefits, and thus these plants may be used for the preparation of nutraceutical compositions. Nutraceutical compositions can be derived from plant tissue. Information about numerous plants and herbs that have been used to prepare nutraceutical compositions has been compiled and is available in publications including the *German Commission E Monographs, Botanical Safety Handbook*, and *HerbalGram*, a quarterly publication of the American Botanical Council which references numerous clinical trials that have been performed using nutraceuticals.

Information on description and constituents, modern uses, dosage (in a variety of forms), actions, contraindications, side effects, interactions with conventional drugs, mode of administration, duration of application, regulatory status, AHPA botanical safety rating, and comments are available for a number of plants and include among others bilberry, cascara, cat's claw, cayenne, cranberry, devil's claw, dong quai, echinacea, evening primrose oil, feverfew, garlic, ginger, ginkgo, Asian ginseng, Siberian ginseng, goldenseal, gotu kola, grape seed, green tea, hawthorn, kava, licorice, milk thistle, saw palmetto, St. John's wort, and valerian.

The actions of these nutraceutical compounds may be fast or/and short-term or may help achieve long-term health objectives. Nutraceutical compositions may comprise dried and ground plant tissue or extracts from these tissues in a pharmacologically acceptable medium as a natural approach for treatment of various ailments. The nutraceutical compositions may be contained in a medium such as a buffer, a solvent, a diluent, an inert carrier, an oil, a creme, or an edible material. The nutraceutical may be orally administered and may be in the form of a tablet or a capsule. Alternatively the nutraceutical may be in the form of an ointment which has extracts of plant tissue in an oil or cream which can be topically applied to the skin.

VII. Definitions

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VIII. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Isolation and Sequence Analysis of *M. truncatula* CYP81E Family Members

A putative CYP81E cDNA was obtained by screening an *M. truncatula* root cDNA library with a licorice I2'H (CYP81E1) probe (Akashi et al., 1998) labeled with $^{32}$P and used to screen a cDNA library according to standard procedures (Stratagene). The cDNA library was constructed from mRNA from developmentally pooled *M. truncatula* root tissue. After two rounds of screening, a full-length cDNA clone (SEQ ID NO:1) was isolated that contained 1732 nucleotides and encoded a 498 amino acid polypeptide with a deduced molecular mass of 57,640 Da (SEQ ID NO:2). It shares about 84% DNA sequence identity with licorice CYP81E1, and encodes a protein classified as MtCYP81E7.

Figure 2:
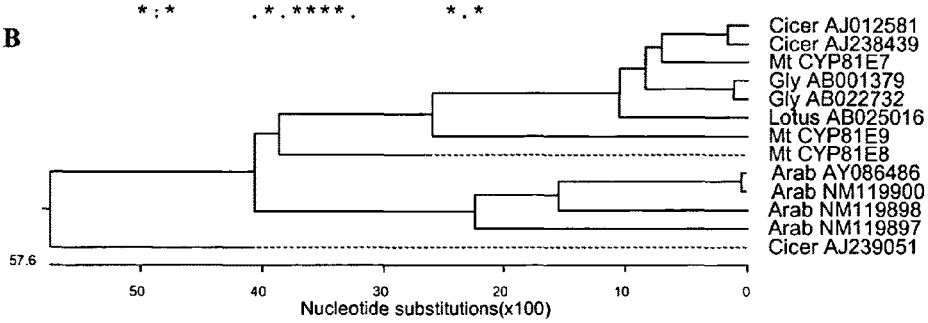
FIG. 2. Sequence comparisons of *M. truncatula* CYP81E family members. A. Protein sequence alignment of MtCYP81E7 (SEQ ID NO:2), E8 (SEQ ID NO:4) and E9 (SEQ ID NO:6). The boxes indicate the proline-rich motif (I) and conserved heme-binding domain (box II) characteristic of P450s. Asterisks show identical amino acid residues and dots indicate similar residues. The N-terminal amino acids shown in italics for CYP81E9 were added in the expression construct. B. Dendrogram of CYP81 family P450 enzymes. Alignment was performed using the Clustal W method in the DNASTAR program. Dashed lines indicate a negative branch length, a common result of averaging.

Using CYP81E1 and MtCYP81E7 cDNA sequences for BLAST analysis of the TIGR *M. truncatula* Gene Index database (www/tigr.org/tgi/) with Matrix at blosum62, Expect at 10 and Description at 20 and all other parameters set at the default, two further CYP81E subfamily candidates were revealed. TC69129, which exists as a full length cDNA in the Noble Foundation's *M. truncatula* EST library collection, contained a 22 bp 5'-untranslated leader sequence, followed by an open reading frame of 1497 bp that encodes a 499 amino acid polypeptide with a deduced molecular mass of 57,301 Da (FIG. 2A). It is 58% identical at the amino acid level to MtCYP81E7 and 60% identical to CYP81E1, and is classified as MtCYP81E8 (SEQ ID NO:5). TC70025 was a partial cDNA sequence that lacks the 5'-untranslated region and the translation start codon; one of its three deduced open reading frames encoded a putative protein of 500 amino acid residues sharing 61% identity with MtCYP81E7 and 65% identity with MtCYP81E8; it is classified as MtCYP81E9 (FIG. 2A) (SEQ ID NO:5).

Sequence analysis was performed using ExPASy Molecular Biology Server tools and DNASTAR, and sequence alignments were done by the CLUSTAL W (1.81) method. In silico expression analysis was performed by counting the EST numbers for the targeted gene (tentative consensus, TC) in each specific library in the MtGI database and normalizing to EST numbers sequenced from that library (see legend to FIG. 6) (Dixon et al., 2002).

Sequence comparison using the Clustal W method in the DNASTAR program showed that MtCYP81E7 clustered with licorice CYP81E1 (Akashi et al., 1998) and homologs from chickpea (Overkamp et al., 2000) and *Lotus japonicus* (Shimada et al., 2000), suggesting that it might encode an I2'H. MtCYP81E9 and MtCYP81E8 are less closely related to MtCYP81E7 and other CYP81E1 members, and represent two separate unique subclasses (FIG. 2B).

*M. truncatula* contains at least three CYP81E family members; one (MtCYP81E7) has similar properties to the I2'H from licorice (Akashi et al., 1998) and one (MtCYP81E9) is an isoflavone 3'-hydroxylase, an enzyme defined biochemically in crude plant extracts (Clemens et al., 1993), but until now not identified at the molecular level. Functional characterization of the third CYP81E enzyme (MtCYP81E8) was not possible.

Example 2

Functional Characterization of MtCYP81E Enzymes in Yeast

The coding regions of MtCYP81E7 and MtCYP81E9 were amplified by PCR and introduced into the yeast expression vector YeDP60 under control of a galactose-inducible and glucose-repressible promoter (Pompon et al., 1996). Because MtCYP81E9 lacks the two N-terminal amino acid residues in its membrane anchor, N-terminal methionine and threonine residues (chosen based on alignments of CYP81E family members) (FIG. 2) were introduced by PCR. The full length CYP81E8 cDNA was directly excised from its original clone in the Noble Foundation EST library collection and ligated into YeDP60.

Figure 3:
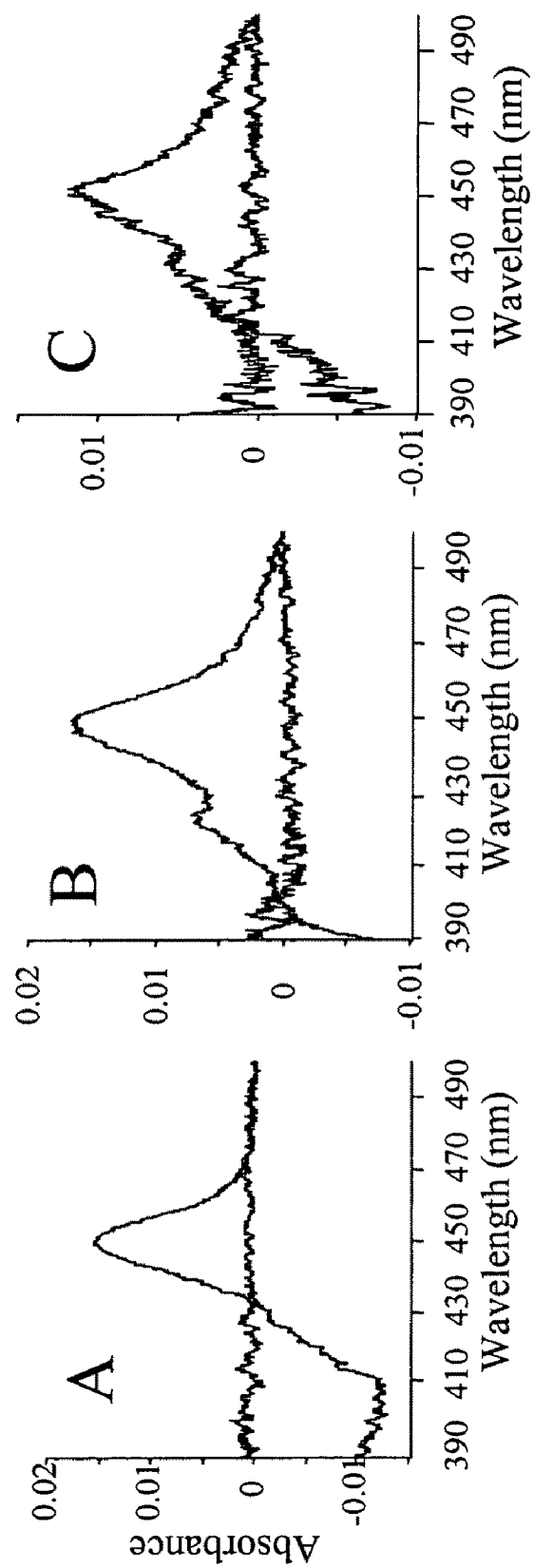
FIG. 3. Carbon monoxide difference spectra of yeast microsomes expressing recombinant MtCYP81E7 (I2'H) (A), MtCYP81E8 (B) and MtCYP81E9 (I3'H) (C). Flat lines represent baseline measurements for reduced microsomes prior to bubbling carbon monoxide.

Expression constructs were transformed into yeast strain WAT11 that carries an *Arabidopsis thaliana* cytochrome P450 reductase gene integrated in its genome. Carbon monoxide difference spectra of reduced microsomal preparations from WAT11 strains harboring each of the three different MtCYP81E constructs exhibited maximum absorbance at 450 nm (FIG. 3), whereas microsomes from strains harboring empty vector lacked the 450 nm peak. The levels of expressed P450 proteins, based on the CO difference spectra, were 269 nmol/g microsomal protein for MtCYP81E7, 278 nmol/g for MtCYP81E8 and 177 nmol/g for MtCYP81E9.

Figure 4:
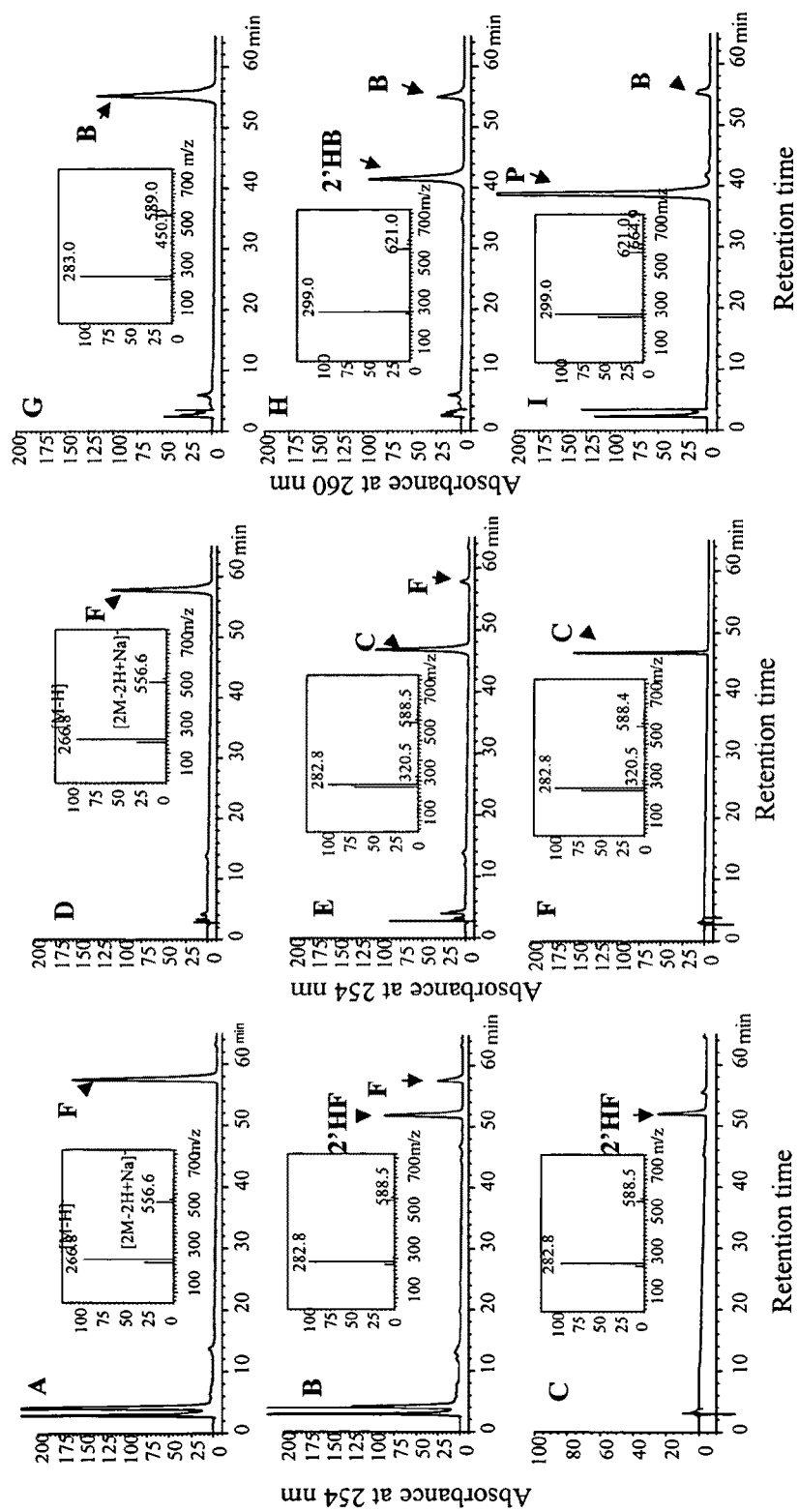
FIG. 4. HPLC-UV and HPLC-MS analysis of products formed by the activity of MtI2'H and MtI3'H on isoflavone substrates. Insets show mass spectra of the major peak (substrate or product). All incubations contain NADPH unless otherwise stated. (A), formononetin incubated with yeast microsomes harboring empty vector. (B), products from incubation of I2'H with formononetin. (C), 2'-hydroxyformononetin standard. (D), formononetin incubated with I3'H in the absence of NADPH. (E), products from incubation of I3'H with formononetin. (F), calycosin standard. (G), biochanin A incubated with microsomes harboring empty vector. (H), products from incubation of I2'H with biochanin A. (I), products from incubation of I3'H with biochanin A. Compounds are: F, formononetin; 2'HF, 2'-hydroxyformononetin; C, calycosin; B, biochanin A; 2'HB, 2'-hydroxybiochanin A; P, pratensein.

Yeast microsomes expressing MtCYP81E7 converted formononetin to 2'-hydroxyformononetin, as confirmed by HPLC with UV diode array detection (retention time (RT) 52.1 min, absorption maxima at 203 nm, 249 nm and 293 nm) and LC-MS (molecular ion at m/z 282.8 (M-H)) as compared to an authentic standard (FIG. 4A-C). MtCYP81E7 converted biochanin A to a product with molecular ion at m/z 299, and absorption maxima at 203 nm, 259 nm and 188 nm (shoulder), consistent with formation of 2'-hydroxybiochanin A (FIG. 4H). Neither product was observed in reactions without NADPH or with microsomes from yeast cells harboring empty vector (FIG. 4 A,G). Therefore, MtCYP81E7 was shown to be an isoflavone 2'-hydroxylase (MtI2'H).

When yeast microsomes expressing MtCYP81E9 were incubated with formononetin, the product (RT 47 min) had a molecular ion at 282.8 m/z, but its UV spectrum showed absorption peaks at 199, 219, 249 and 291 nm, identical to an authentic sample of calycosin (3'-hydroxyformononetin) (FIGS. 4E,F). The product formed from biochanin A by recombinant MtCYP81E9 had a UV spectrum with maximum absorption at 262 nm and two shoulders at 290 and 330 nm, in good agreement with the reported spectrum of pratensin (Mabry et al., 1970) (FIG. 4I). Therefore, MtCYP81E9 was shown to be an isoflavone 3'-hydroxylase (MtI3'H).

MtI2'H and MtI3'H show preference for the 5-hydroxy-substituted biochanin A over its corresponding 5-deoxy derivative formononetin (Table 1). MtI2'H was also active with pseudobaptigenin (Table 1), converting it into a major product with molecular ion at 290 m/z and UV absorption maxima at 245 and 305 nm, consistent with 2'-hydroxypseudobaptigenin. Similar to licorice I2'H, MtI2'H had weak activity with daidzein and genistein (5,7,4'-trihydroxyisoflavone), and negligible activity with 2'-hydroxyformononetin and calycosin (Table 1). Daidzein and genistein were converted to both 2'- and 3'-hydroxylated products, with preference for 2'-hydroxylation. In contrast, MtI3'H had low activity with pseudobaptigenin or daidzein, but was more active with 2'-hydroxyformononetin, with the major product tentatively identified as the oxidation product of 2',3'-dihydroxyformononetin. Neither enzyme hydroxylated the 7-O methylated isoflavonoids isoformononetin and prunetin.

TABLE 1

Substrate specificity of I2'H and I3'H

| Isoflavone (40 µM) | I2'H (MtCYP81E7) | I3'H (MtCYP81E9) |
|---|---|---|
| Biochanin A | 100% | 100% |
| Formononetin | 37.2% | 50% |
| Pseudobaptigenin | 35% | 7.6%[a] |
| Daidzein | 18.6%[a] | 1.73%[a] |
| Genistein | 10.2%[a] | 19.13%[a] |
| 2'-Hydroxyformononetin | 9.1%[a] | 39.34%[b] |
| 3'-Hydroxyformononetin | 4.7% | ND |
| Isoformononetin | ND | ND |
| Prunetin | ND | ND |
| 6,7,4'-Trihydroxyisoflavone | ND | ND |
| 3',4',7-Trihydroxyisoflavone | ND | ND |

[a]Sum of putative 2' and/or 3'-hydroxylated products.
[b]Sum of all the products (multiple product peaks on HPLC).
ND, activities not detectable.

100%, 53.75 mol pmol$^{-1}$ protein h$^{-1}$ for 2'-hydroxylation and 98.56 pmol pmol$^{-1}$ protein h$^{-1}$ for 3'-hydroxylation When assayed under standard assay conditions, or at different pH values and NADPH concentrations, recombinant MtCYP81E8 exhibited no activity with any of the above described isoflavones, or with flavonoids including narigenin, liquiritigenin, apigenin, luteolin or kaempferol.

The MtI2'H and MtI3'H exhibited strong preference for substrates with a 4'-methoxy substitution on the B-ring, consistent with the placing of isoflavone hydroxylation after 4'-O-methylation, a reaction that is tightly linked to the production of isoflavone from flavanone (naringenin or liquiritigenin) catalyzed by IFS (Liu and Dixon, 2001; Akashi et al., 2003). Indeed, most isoflavonoids in *Medicago* species are methoxy-substituted on the 4'-position. However, these compounds generally lack a hydroxyl group on the 5-position of the A-ring, resulting from the action of a specific chalcone reductase earlier in the pathway (Dixon, 1999), and it is therefore interesting that both I2'H and I3'H preferred biochanin A (5-hydroxyformononetin) to formononetin. This preference, which is consistent with the observed specificity of hydroxylases in crude extracts from *Cicer arietinum* cell cultures (Hinderer et al., 1987), may simply reflect active site chemistry rather than indicate the operation of a major pathway leading to 5-hydroxy-substituted isoflavonoids in *M. truncatula*.

Both CYP81E hydroxylases from *M. truncatula* were unable to hydroxylate the 7-methoxyisoflavones isoformononetin and prunetin. A similar situation occurs with flavonoid 6-hydroxylase (CYP71D) from soybean, for which a free 7-hydroxyl group is essential both for anchoring the substrate and maintaining the 6-carbon of the A-ring in the spatially correct position for catalysis (LatundeDada et al., 2001). The lack of activity of I2'H and I3'H with isoformononetin is important because the isoflavone O-methyltransferase (IOMT) from *Medicago* paradoxically converts daidzein to isoformononetin in vitro. The lack of detection of isoformononetin in *Medicago*, and its inability to be subsequently hydroxylated, confirms previous conclusions that isoformononetin is not an in vivo product of IOMT (Liu and Dixon, 2001).

Example 3

Kinetic Properties of MtI2'H and MtI3'H

The kinetic properties of recombinant MtI2'H (MtCYP81E7) and MtI3'H (MtCYP81E9) were analyzed. The enzymes were found to have similar pH profiles, with optima around pH 8.0. The apparent KM value of MtCYP81E7 for NADPH was about 0.17 µM, consistent with the values observed for many P450 enzymes (Mihaliak et al., 1993). KM values of MtCYP81E7 for formononetin and biochanin A at 2 mM NADPH and pH 8.0 were 67 and 51 µM, respectively, with Kcat values of 0.015 s-1 and 0.033 s-1. Under the same conditions, KM values of MtCYP81E9 were 49.7 µM for formononetin and 112.6 µM for biochanin A, with Kcat values of 0.028 s-1 and 0.1 s-1, respectively.

Example 4

Expression of MtI2'H in *Arabidopsis thaliana*

*A. thaliana* was transformed with a construct containing the MtI2'H (MtCYP81E7) open reading frame under control of the constitutive cauliflower mosaic virus 35S promoter. Transformation and selection of transgenic plants was as previously described (Liu et al., 2002). The full length MtI2'H cDNA was removed from the original pBSK clone by digestion with EcoRI and KpnI and inserted into the shuttle vector pRTL2. After digestion with HindIII, the chimeric gene under control of the cauliflower mosaic virus 35S promoter was moved into the binary vector pCAMBIA3300.

Leaves from I2'H transgenic plant #33-2-5 and empty vector control line #33-00 were cut at the lower petiole and allowed to stand in the wells of 96 well tissue culture plates containing a solution of formononetin (2 mM) in DMSO: methanol: $H_2O$ (1:1:2). The cut leaves were incubated at 22° C. under greenhouse conditions for 2 h and then exhaustively washed with dd$H_2O$. The collected leaves were frozen in liquid N2 prior to extraction of phenolic compounds and analysis by HPLC with the procedure and gradient II described previously (Liu and Dixon, 2001).

Figure 5:
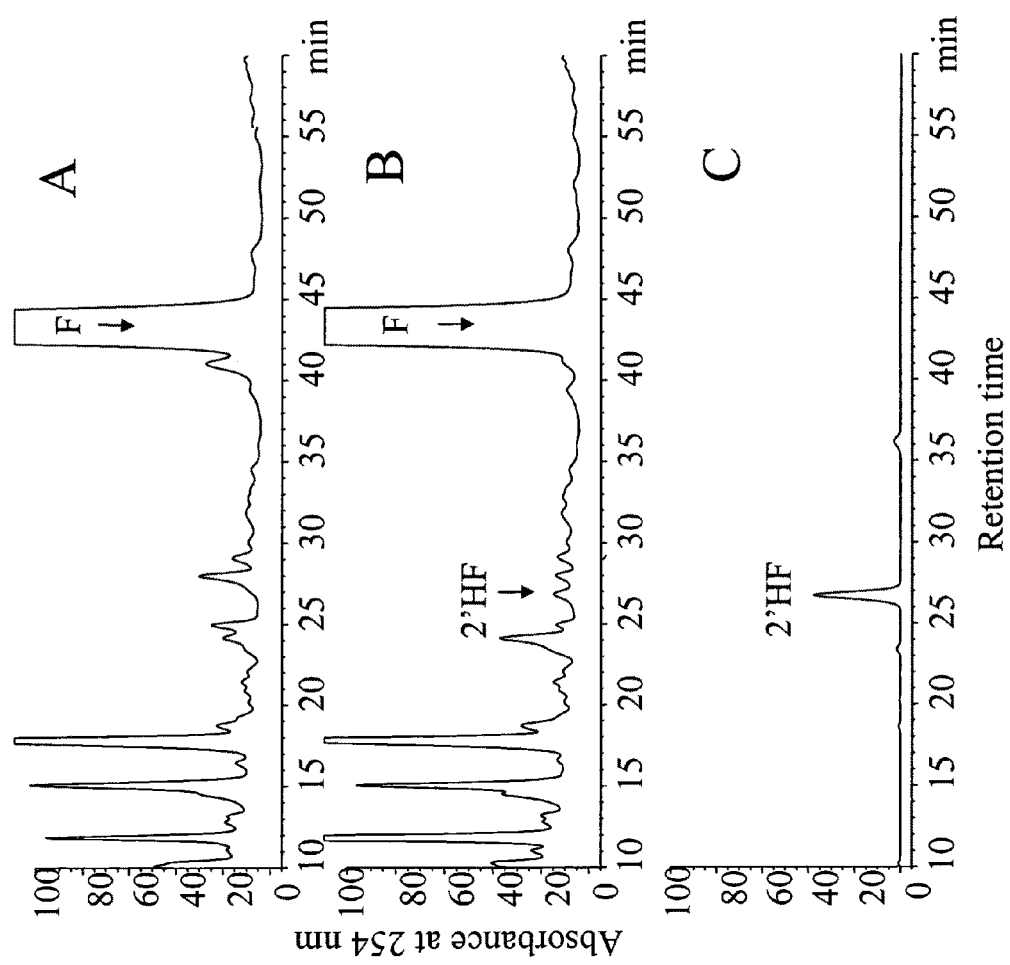
FIG. 5. *M. truncatula* I2'H is functional in *Arabidopsis*. Leaf extracts from control (A) and I2'H transgenic line 33-2-5 (B) were analyzed by HPLC after feeding formononetin (F).

After selection for phosphinothricin resistance and RNA gel blot confirmation of transformants, the leaves of transgenic and control plants were collected and fed formononetin. Extracts from MtI2'H transgenic plants, but not from control plants, contained 2'-hydroxyformononetin, as determined by HPLC with diode array detection and comparison with authentic standards (FIG. 5).

Example 5

Subcellular Transient Localization of MtI2'H and MtI3'H in Alfalfa Leaves

To determine the subcellular localization of MtI2'H and MtI3'H, MtI2'H::EGFP and MtI3'H::EGFP fusion proteins were created by in-frame N-terminal ligation to enhanced green fluorescent protein (eGFP). After bombarding constructs into young alfalfa leaves, the distribution of fluorescence was observed by confocal microscopy. Both MtI2'H:: EGFP and MtI3'H::EGFP fusion proteins had a reticulate distribution pattern with localization around, but not within, the nucleus. The fluorescent spots clearly visible in FIG. 6C are aggregates of the GFP-fusion protein caused by the high level of expression. They are clearly distinguishable from the larger fluorescent region representing the nucleus when examined in a set of serial sections. A perinuclear and reticulate distribution was also observed for the eGFP fusion protein of isoflavone synthase (IFS, CYP93C2) and for the ER marker protein mGFP-HDEL in alfalfa leaves (Liu and Dixon, 2001), whereas the fluorescence of free GFP appears diffusely in the cytosol and is also localized within the nucleus.

The results confirm that both I2'H and I3'H localize to the membranes of the endoplasmic reticulum, as shown by confocal microscopy of cells expressing isoflavone hydroxylase-GFP fusions. Identical cellular localization is shown by the IFS cytochrome P450 and IOMT in alfalfa (Liu and Dixon, 2001). Further studies, such as fluorescence energy resonance transfer (FRET), will confirm whether isoflavone hydroxylases are physically associated in complexes with IFS on the ER membranes.

Example 6

Tissue-Specific and Stress-Inducible Expression of MtI2'H and MtI3'H

An overview of isoflavone hydroxylase expression patterns was initially obtained by in silico analysis of EST numbers in various *M. truncatula* EST libraries available through the TIGR *M. truncatula* gene index (Dixon et al., 2002). The distribution of MtI2'H and MtI3'H transcripts was quite distinct. MtI2'H transcripts were found to be strongly expressed in root tissues and in leaves infected with the fungus *Phoma medicaginis*, whereas MtI3'H transcripts were present at low levels in leaves (control and subjected to insect herbivory), but found in root tissues only after arbuscular mycorrhizal colonization (FIG. 6A). The highest levels of transcripts corresponding to the unidentified MtCYP81E8 appeared to be present in fungally infected leaves.

High stringency RNA gel blot analyses (FIG. 6B-F) confirmed that MtI2'H (MtCYP81E7) transcripts accumulated constitutively in roots, but were present at very low levels in uninfected stems and leaves, whereas MtI3'H (MtCYP81E9) was expressed constitutively in stems and leaves but not in roots (FIG. 6B). Exposure of seedlings to drought strongly reduced MtI2'H expression in roots, and slightly increased MtI3'H expression in leaves (FIG. 6C). Exposure of leaves to copper chloride (an elicitor of medicarpin production in alfalfa) had no effect on MtI2'H but weakly induced I3'H transcript levels, whereas exposure to methyl jasmonate induced MtI3'H but not MtI2'H (FIG. 6C). A similar induction of MtI3'H was observed in leaves exposed to herbivory from beet armyworm caterpillars (FIG. 6E). Infection of leaves with the leaf spot fungus *Phoma medicaginis* resulted in a strong induction of MtI2'H (FIG. 6D). Although I3'H transcript levels also increased following infection with *Phoma*, a similar increase was observed in the control plants; thus, the procedures used for infection (wounding with a pin wheel followed by placing plants in a polythene bag under high humidity) appear to cause stress that induced I3'H, but not I2'H. Finally, MtI2'H was induced by exposure of cell cultures to yeast elicitor, a treatment that did not induce MtI3'H (FIG. 6F).

*M. truncatula* contains at least three IFS genes (Dixon et al, 2002). RNA gel blot analysis confirmed expression of one or more IFS genes in all tissues in which either I2'H or I3'H were expressed.

Example 7

Accumulation of Isoflavonoids in *M. truncatula*

The constitutive expression of I2'H in roots, and elicitor/infection-inducible expression in leaves or cell cultures, is consistent with the accumulation patterns of the 2'-hydroxyisoflavone derived medicarpin malonyl glucoside (constitutive) and medicarpin aglycone (inducible phytoalexin) in alfalfa (Dixon, 1999). HPLC analysis confirmed the accumulation of formononetin and medicarpin, as well as glycosides of these compounds, in fungal infected leaves of *M. truncatula*. Neither compound was detected in leaves exposed to MeJA or insect herbivory. The 3'-hydroxylated isoflavonoids such as pseudobaptigenin or maackiain could not be detected (detection limit 3.5 nmol/g fresh weight by our HPLC procedure) in *M. truncatula* leaves exposed to insect herbivory or MeJA treatment, although new compounds eluting at 61.5 min, 62 min and 63.7 min were observed. The nature of these compounds is currently under investigation.

Example 8

Materials and Methods

A. Chemicals

Isoformononetin, 2'-hydroxyformononetin, 3'-hydroxyformononetin (calycosin) and pseudobaptigenin were purchased from Apin (Abingdon, UK). Maackiain and pisatin were kindly provided by Dr. H. D. VanEtten, (University of Arizona, Tucson). Maackiain glucoside and maackiain glucose malonate standards were gifts from Dr. S. Tebayashi (Kochi University, Japan). Medicarpin was from a lab collection. Other isoflavonoids were from Indofine Chemical Company (Somerville, N.J.). CO was obtained from Aldrich and all other chemicals were from Sigma (St. Louis, Mo.).

B. Plant Materials and Treatments

*Medicago truncatula* (Jemlong A17) plants were grown in sand at 22° C., under a 16 h light/8 h dark regime and at 50% humidity in a growth chamber for 42 days. The plants were watered once a day and fertilized twice a week. Young shoots were cut at the second nodes and the upper portions allowed to stand in aqueous 0.33 mM copper chloride solution for 12 h or 500 µM methyl jasmonate for 48 h; control plants were placed in water along with the treated samples and incubated for the same times. Drought stress treatments were imposed by withholding watering for 5 days under the same growth conditions; control plants were of the same age but watered normally. Harvested roots, leaves, and stems from plants of the same developmental age were frozen in liquid N2 and stored at −80° C. prior to RNA extraction or metabolite analyses.

*Phoma medicaginis* was streaked on PDA medium plates and grown at 28° C. for about 20 days. Fungal spores were collected by washing with 0.2% Tween in ddH$_2$O. Leaves pre-selected for fungal infection were wounded with a tracing wheel (He and Dixon, 2000) and the selected leaves on the intact plants sprayed with *Phoma* spore solution (1.3×10$^7$/ml), covered with a plastic bag, and grown in the growth chamber. Leaves from control plants were treated identically except for the lack of fungus.

For insect herbivory studies, 4th instar larvae of beet armyworm (*Spodoptera exigua*) were allowed to feed overnight on the leaves of nine-week-old plants growing in a growth chamber. The damaged leaves were collected for analysis. Control leaves were collected from the same plant before exposure to larvae.

*M. truncatula* cell suspension cultures were initiated from root callus and maintained in Schenk and Hildebrandt medium at 24° C. in the dark as described previously (Dalkin et al., 1990). The cells were subcultured every 15 days. Cells were treated with yeast elicitor (Schumacher et al., 1987) 12 days after subculture at a final concentration of 50 μg glucose equivalent/ml culture. Cells were collected by vacuum filtration through a nylon mesh, washed with ddH$_2$O, and frozen in liquid N2.

C. Expression of *Medicago* CYP81E in Yeast

The open reading frame of MtCYP81E7 was amplified with forward primer AACGGATCCATGGGAATCCTTTC (SEQ ID NO:7) and reverse primer GAACGGTACCTTAGATGAATTAC (SEQ ID NO:8), which introduced BamHI and KpnI restriction sites respectively. The BamHI site in the original clone was eliminated by mutation of the third nucleotide (G to A) in the second translated codon after the ATG start site. The PCR reaction was performed at 94° C. for 3 min, then 94° C. for 45 s, 53° C. for 45 s, and 72° C. for 1 min, for a total of 35 cycles using a mixture of high fidelity pfu and Taq (1:2) DNA polymerase.

MtCYP81E9 was amplified with the forward primer AACGGATCCATGACCTTATTCTATTACTC (SEQ ID NO:9) and the reverse primer AACAGGTACCTCACTTCGTTACATCA (SEQ ID NO:10). Since the MtCYP81E9 clone apparently lacked nucleotides encoding two amino acid residues at the N-terminus (within the membrane anchor) an ATG start codon and a codon encoding threonine (indicated in italics in FIG. 2A) were introduced based on alignments of the three *M. truncatula* putative CYP81E family members. PCR was performed as for MtCYP81E7, except the annealing temperature was 54° C.

PCR products were digested with BamHI and KpnI and ligated into the yeast expression vector YeDP60 following BamHI/KpnI digestion. MtCYP81E8 was directly excised from the original clone in pBSK(+) by BamHI and KpnI and inserted into YeDP60. All constructs were sequenced to ensure that there were no PCR-introduced errors. The constructs were then transferred into yeast (*Saccharomyces cerevisiae*) strain WAT11 with a chromosomally integrated *Arabidopsis* NADPH: cytochrome P450 reductase gene (Pompon et al., 1996) by the LiAc method (Gietz et al., 1992), and transformants selected on SDI media (Pompon et al., 1996). Incubation of yeast cultures and induction of protein expression were performed using the high-density procedure (Pompon et al., 1996). After induction with 20% galactose for ~18 h, yeast cells was harvested, weighed, and immediately processed for microsomal fractionation.

D. Preparation of Yeast Microsomes

Disruption and sub-cellular fractionation of yeast cells were performed with a modified procedure that combined mechanical rupture and enzymatic lysis methods in order to improve fractionation efficiency. Harvested yeast cells (usually 9~11 g cell pellet from 1 liter of *S. cerevisiae* cell culture) were washed with TEK buffer (50 mM Tris-HCL pH 7.5, 1 mM EDTA, 0.1 M KCl) once briefly then re-suspended in 2 vols of Zymolyase buffer A (50 mM Tris-HCl pH 7.5 10 mM MgCl$_2$, 1 M sorbitol, 30 mM DTT), incubated at room temperature for 15 min, centrifuged at 6500 rpm for 5 min, and re-suspended in an equal volume of Zymolase buffer B (same as Zymolyase buffer A except for DTT at 1 mM). Zymolyase 100T from *Arthrobacter luteus* (200 U/ml, Seikagaku, Tokyo) was then added.

After incubation at ~80 rpm for 30 to 40 min, spheroplasts were centrifuged down for 5 min, washed twice with Zymolyase buffer B, and then twice with phosphate buffer A (0.1 M potassium phosphate pH 8.0, 1 M sorbitol, 14 mM 2-mercaptoethanol). The spheroplasts were re-suspended in a minimum vol of phosphate buffer B (0.1 M potassium phosphate pH 8.0, 0.4 M sucrose, 14 mM β-mercaptoethanol, 1 mM PMSF and 1× protein inhibitor cocktail (Roche Diagnostics GmbH, Mannheim, German), and 1 vol of glass beads (diameter at 0.45/0.50 mm) was added. Samples were vigorously vortexed at 4° C., with the quality of cell disruption checked under the microscope. The supernatant was then removed and the beads washed four times with phosphate buffer B. Supernatants were pooled and centrifuged at 12,000 g for 10 min; the resulting supernatant was then ultracentrifuged at 140,000 g for 90 min. The supernatant was discarded and the pellet washed briefly with phosphate buffer C (0.1 M potassium phosphate, pH 8.0, 0.4 M sucrose, 0.5 mM glutathione), and re-suspended in the same buffer plus 5% glycerol at about 12 mg total protein/ml. Protein was quantified using a Bio-Rad protein assay kit (Bio-Rad, Hercules, Calif.).

E. Carbon Monoxide (CO) Difference Spectra of Microsomes and Assay of Hydroxylase Activities CO difference spectra of microsomes were obtained by the method of Mihaliak and Croteau (Mihaliak et al., 1993) using a Shimatzu UV-2401PC split beam spectrophotometer. Briefly, microsomal preparations (~1 mg/ml total protein) in 0.1 M phosphate buffer C were mixed with a few mg of solid Na$_2$S$_2$O$_4$ and equal volumes of this preparation distributed equally into sample and reference cuvettes. The baseline was recorded and CO gently bubbled through the sample cell for a few min prior to recording the difference spectrum from 390-500 nm. An extinction coefficient of 91 cm-1 mM-1 (A450 minus A490) was used to calculate the cytochrome P450 concentration.

Hydroxylase assays were performed in phosphate buffer C in a total volume of 150 μl containing 2 mM NADPH, 40 μM isoflavone substrate and 40~70 pmol P450 protein. Reactions were incubated at 25° C. for 1.5 h (over which period the reactions were linear) with gentle shaking and stopped by extracting twice with 500 μl of ethyl acetate. The extracts were combined, evaporated under N$_2$, re-suspended in 60 μl of methanol, and analyzed by HPLC or LC-MS. All assays to determine enzyme specificity were carried out in duplicate. For kinetic studies, the isoflavone concentration was varied at a fixed concentration of NADPH (2 mM), and kinetic constants calculated from initial rate data using Lineweaver-Burke double reciprocal plots. All kinetic analyses were carried out in triplicate.

F. Analysis of Enzymatic Products by HPLC-UV and HPLC-MS

Reaction products from enzyme assays (30 μl) were analyzed by HPLC. Samples were applied to an ODS2 reverse phase column (5 μm particle size, 4.6×250 mm) and eluted in 1% phosphoric acid with an increasing concentration gradient of acetonitrile of 0-5 min, 5%; 5-10 min, 5-10%; 10-15 min, 10-15%; 15-20 min, 15%; 20-25 min, 15-17%; 25-30 min, 17-23%; 30-65 min, 23-50%) at a constant flow rate of 0.8 ml/min. UV absorption was monitored at 235, 254, 287 and 310 nm with a photodiode array detector. When biochanin A and prunetin were used as substrates, the products were resolved with the acetonitrile gradient described previously (Liu et al., 2002).

Product identification was firstly based on comparisons of chromatographic behavior and UV spectra with authentic standards. Identifications were then confirmed by HPLC-MS, using a HP 1100 liquid chromatograph coupled to a Bruker Esquire Ion-Trap mass spectrometer equipped with an electrospray source. HPLC separation was achieved using a J. T. Baker Bakerbond reverse-phase column (C18, 5 µm, 4.6 mm×250 mm, J. T. Baker, Philipsberg, N.J.). Samples were eluted with the gradient described above but with 0.1% aqueous acetic acid replacing the 1% phosphoric acid. Ion charge control was set at 30,000 with a max acquire time of 100 ms. Mass spectra were recorded over a range of 50-2200 m/z.

G. RNA Extraction and Gel Blot Analysis

Total RNA was isolated from about 1 g of treated plant material with the Tri-reagent extraction kit following the manufacturer's protocol (MRC Inc., Cincinnati, Ohio). Twenty µg RNA was loaded per lane, resolved by electrophoresis on a 1% agarose gel, and transferred to Hybond-H+ nylon membrane. RNA blots were developed using either 32P-labeled probes (for insect herbivory and elicited cell culture samples) or the ECL non-radioactive system. For radioactive detection, blots were probed with MtI2'H or MtI3'H full-length cDNA in Church buffer (Church and Gilbert, 1984) at very high stringency (68° C.). The hybridized membranes were washed at high stringency using phosphate buffer 1 (40 mM NaHPO$_4$ pH 7.2, 5% SDS, 1% BSA) and buffer 11 (40 mM NaHPO$_4$ pH 7.2, 1% SDS) twice respectively at 68° C. and finally exposed to phosphorimaging or X-ray film. RNA loading was monitored by ethidium bromide staining. For analysis of blots with the ECL direct nucleic acid labeling and detection system (Amersham Biosciences, Little Chalfont, Buckinghamshire, UK), MtCYP81E7, MtCYP81E9 and Mt 18S RNA probes were labeled with horseradish peroxidase following the manufacturer's procedure. Hybridization and washing were performed at 42° C., and the images were developed using detection reagents containing hydrogen peroxide and luminol. X-ray film was exposed to the blots for 1 to 30 min. The triplicate RNA blots (using two separate tissue samples) gave essentially the same results.

H. Extraction and Analysis of Isoflavonoids from *M. truncatula*

Phenolic compounds were extracted using pre-cooled acetone and acetone: methanol, hydrolyzed with β-glucosidase, and partitioned into ethyl acetate as described previously (Liu and Dixon, 2001). Alternatively, extraction was performed according to Higgins (1972) using 95% ethanol and partitioning of the β-glucosidase digest into chloroform. Extracts were dried and then re-dissolved in methanol for HPLC analysis. Chromatography was by the same procedure described above for analysis of enzymatic products.

I. Construction and Transient Expression of Chimeric eGFP Fusion Genes

To create fusion proteins of MtI2'H and MtI3'H with eGFP, the coding region sequence of eGFP containing the multiple restriction sites was moved from pEGFPN-1 (Clontech, Palo Alto, Calif.) by digestion with EcoRI and XbaI to the shuttle vector pRTL2 (Restrepo et al., 1990), generating eGFP expression vector pRTLGFP. The MtI2'H open reading frame was amplified using pfu DNA polymerase (Stratagene, La Jolla, Calif.) with the forward primer 5'CAAACGGTAC-CATGGGGATC3' (SEQ ID NO:11) and the reverse primer 5'ATGAGGTACCTTGAAAACCTTG3' (SEQ ID NO:12). The MtI3'H coding region was amplified using the forward primer 5'GACGGTACCATGACCTTATTCTATTACT3' (SEQ ID NO:13) and the reverse primer 5'GACGGATCCT-TCGTTACATCATTGGCTA3' (SEQ ID NO:14). All PCR products were sequenced to ensure that they did not contain errors. The MtI2'H fragment was ligated into KpnI-digested pRTLGFP (the orientation being determined by PCR with a universal pRTL2 primer and reverse MtI2'H primer), and the MtI3'H fragment was inserted into BamHI/KpnI-digested pRTLGFP.

The procedure for transient expression of chimeric genes encoding MtI2'H- and MtI3'H-GFP fusions in alfalfa (cv Regen SY) leaves, and confocal microscopy for detection of green fluorescence localization, was as previously described (Liu and Dixon, 2001).

Example 9

Identification of Additional Isoflavone Hydroxylase Sequences

A search was carried out in the NCBI translated database (tblasn) to identify isoflavone 2'hydroxylase and isoflavone 3'hydroxylase sequences using the full length I3'H protein sequence as the query. The search parameters were blast set at default parameter with Expect at 10, Matrix set at Blousum62, Gap costs at Existence 11, Extension 1, and Filter set at low complexity. Among 188 total hits the best hits were selected and are listed below.

TABLE 2

Additional Isoflavone Hydroxylase Sequences

| Selected hits | (bits) Value |
|---|---|
| gi|37726103|gb|AY166658.1| *Pisum sativum* cytochrome P450 mR. (SEQ ID NO: 15) | 6780.0 |
| gi|33521520|gb|AY278229.1| *Medicago truncatula* CYP81E8 mRNA (SEQ ID NO: 16) | 578 e-163 |
| gi|3850629|emb|AJ012581.1|CAR012581 *Cicer arietinum* mRNA (SEQ ID NO: 17) | 575 e-162 |
| gi|4688639|emb|AJ238439.1|CAR238439 *Cicer arietinum* mRNA (SEQ ID NO: 18) | 573 e-162 |
| gi|2443347|dbj|AB001379.1| *Glycyrrhiza echinata* CYP81E1 mRNA (SEQ ID NO: 19) | 572 e-161 |
| gi|4200043|dbj|AB022732.1| *Glycyrrhiza echinata* CYP Ge-31 mRNA (SEQ ID NO: 20) | 570 e-160 |
| gi|7415995|dbj|AB025016.1| *Lotus corniculatus var. japonicus* mRNA (SEQ ID NO: 21). | 565 e-159 |

\* \* \*

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,535,060
U.S. Pat. No. 5,302,523
U.S. Pat. No. 5,322,783
U.S. Pat. No. 5,384,253
U.S. Pat. No. 5,464,765
U.S. Pat. No. 5,508,184
U.S. Pat. No. 5,538,877
U.S. Pat. No. 5,538,880
U.S. Pat. No. 5,545,818
U.S. Pat. No. 5,550,318
U.S. Pat. No. 5,563,055
U.S. Pat. No. 5,591,616
U.S. Pat. No. 5,610,042
Abdullah et al., *Biotechnology*, 4:1087, 1986.
Adlercreutz and Mazur, *Ann. Med.* 29:95-120, 1997.
Akashi et al., *Biochem. Biophys. Res. Comm.* 251:67-70, 1998.
Akashi et al., *Plant Cell Physiol.* 44:103-112, 2003.
Bates, *Mol. Biotechnol.*, 2(2):135-145, 1994.
Battraw and Hall, *Theor. App. Genet.*, 82(2):161-168, 1991.
Bevan et al., *Nucleic Acids Research*, 11(2):369-385, 1983.
Bhandari et al., *J. Chem. Soc. Perkin Trans.*, 839-849, 1992.
Bhattachardee; An; Gupta, *J. Plant Bioch. and Biotech.* 6, (2):69-73. 1997.
Bower et al., *The Plant Journal*, 2:409-416. 1992.
Buising and Benbow, *Mol Gen Genet*, 243(1):71-81. 1994.
Callis, Fromm, Walbot, *Genes Dev.*, 1:1183-1200, 1987.
Casa et al., *Proc. Nat'l Acad. Sci. USA*, 90(23):11212-11216, 1993.
Chandler et al., *The Plant Cell*, 1:1175-1183, 1989.
Choudhary et al., *Plant Cell Rep.*, 9:42-46, 1990.
Chu et al., *Scientia Sinica*, 18:659-668, 1975.
Church and Gilbert, *Proc. Natl. Acad. Sci. USA*, 81:65-71, 1984.
Clemens and Barz, *Phytochemistry*, 41:457-460, 1996.
Clemens et al., *Phytochemistry*, 32:653-657, 1993.
Conkling et al., *Plant Physiol.*, 93:1203-1211, 1990.
Dalkin et al., *Plant Physiol.*, 92:440-446, 1990.
DE 3642 829
De Block et al., *The EMBO Journal*, 6(9):2513-2518, 1987.
De Block, De Brouwer, Tenning, *Plant Physiol.*, 91:694-701, 1989.
Dellaporta et al., In: *Chromosome Structure and Function: Impact of New Concepts, 18th Stadler Genetics Symposium*, 11:263-282, 1988.
Dewick and Martin, *Phytochemistry*, 18:591-596, 1979.
Dewick and Ward, *Phytochemistry*, 17:1751-1754, 1978.
Dewick, In: *The Flavonoids: Advances in Research Since 1986.*, Harborne (Ed.), London: Chapman and Hall, 117-238, 1993.
Dixon and Ferreira, *Phytochemistry*, 60:205-211, 2002.
Dixon and Sumner, *Plant Physiol.*, 131:878-885, 2003.
Dixon et al., *Mol. Plant. Pathol.*, 3:371-390, 2002.
Dixon, In: *Comprehensive Natural Products Chemistry*, Vol. 1, Sankawa (Ed.), Elsevier, Oxford, 773-823, 1999.
Drewes et al., *Phytochemistry.* 59:739-747, 2002.
Ebert et al., 84:5745-5749, *Proc. Nat'l Acad. Sci. USA*, 1987.
EPA App. 154,204, 1985
Fraley et al., *Bio/Technology*, 3:629-635, 1985.
Fromm et al., *Nature*, 319:791-793, 1986.
Gallie et al., *The Plant Cell*, 1:301-311, 1989.
Gelvin et al., In: *Plant Molecular Biology Manual*, 1990.
Ghosh-Biswas et al., *J. Biotechnol.*, 32(1):1-10, 1994.
Gietz et al., *Nucleic Acid Research*, 20:1425, 1992.
Gunia et al., *Z. Naturforsch.* 46:58-66, 1991.
Hagio, Blowers, Earle, *Plant Cell Rep.*, 10(5):260-264, 1991.
Haseloff et al., *Proc. Natl. Acad. Sci. USA*, 94(6):2122-2127, 1997.
He and Dixon, *Plant Cell*, 12:1689-1702, 2000.
He et al., *Plant Cell Reports*, 14 (2-3):192-196, 1994.
Hensgens et al., *Plant Mol. Biol.*, 22(6):1101-1127, 1993.
Hiei et al., *Plant. Mol. Biol.*, 35 (1-2):205-218, 1997.
Higgins, *Physiol. Plant Pathol.*, 2:289-300, 1972.
Hinchee et al., *Bio/technol.*, 6:915-922, 1988.
Hinderer et al., *FEBS Lett.* 214:101-106, 1987.
Hudspeth and Grula, *Plant Mol. Biol.*, 12:579-589, 1989.
Ikuta et al., *Bio/technol.*, 8:241-242, 1990.
ILDIS (International Legume Database and Information Service), In: *Phytochemical Dictionary of the Leguminosae*. Vol. 1, Bisby (Eds.), London: Chapman and Hall, 1994.
Ingham, In: *Phytoalexins*, Bailey and Mansfield, (Eds.), New York: Halstead Press, 21-80, 1982.
Ishidia et al., *Nat. Biotechnol.*, 14(6):745-750, 1996.
Kaeppler et al., *Plant Cell Reports* 9: 415-418, 1990.
Kaeppler, Somers, Rines, Cockburn, *Theor. Appl. Genet.*, 84 (5-6):560-566, 1992.
Katz et al., *J. Gen. Microbiol.*, 129:2703-2714, 1983.
Klee, Yanofsky, Nester, *Bio-Technology*, 3(7):637-642, 1985.
Knittel, Gruber; Hahne; Lenee, *Plant Cell Reports*, 14(2-3): 81-86, 1994.
Kochs and Grisebach, *Arch. Biochem. Biophys.*, 273:543-553, 1989.
Kochs and Grisebach, *Eur. J. Biochem.*, 155:311-318, 1986.
Lambert et al., *Phytochemistry*, 34:1515-1520, 1993.
LatundeDada et al., *J. Biol. Chem.*, 276:1688-1695, 2001.
Lawton et al., *Plant Mol. Biol.* 9:315-324, 1987.
Lazzeri, *Methods Mol. Biol.*, 49:95-106, 1995.
Liu and Dixon, *Plant Cell*, 13:2643-2658, 2001.
Liu et al., *Proc. Natl. Acad. Sci. USA*, 99:14578-14583, 2002.
Mabry et al., In: *The systematic identification of the flavonoids*. New York: Springer-Verlag, 1970.
Mackenbrock and Barz, *Z. Naturforsch.* 38:708-710, 1983.
Mackenbrock et al., *J. Plant Physiol.*, 142:385-391, 1993.
McCabe, Martinell, *Bio-Technology*, 11(5):596-598, 1993.
McCormac et al., *Euphytica*, v. 99 (1) p. 17-25: 1998.
Mihaliak et al., *Meth. Plant Biochem.*, 9:261-279, 1993.
Murakami et al., *Mol. Gen. Genet.*, 205:42-50, 1986.
Murashige and Skoog, *Physiol. Plant.*, 15:473-497, 1962.
Nagatani et al., *Biotech. Tech.*, 11 (7):471-473, 1997.
Nicholas et al., *Phytochemistry*, 24:2881-2883, 1985.
Odell et al., *Nature*, 313:810-812, 1985.
Ogawa et al., *Sci. Rep.*, 13:42-48, 1973.
Olah and Sherwood, *Phytopathology*, 61:65-69, 1971.
Omirulleh et al., *Plant Mol. Biol.*, 21(3):415-428, 1993.
Overkamp et al., *Plant Sci.*, 155:101-108, 2000.
Ow et al., *Science*, 234:856-859, 1986.
PCT App. WO 92/17598
PCT App. WO 94/09699
PCT App. WO 95/06128
PCT App. WO 97/04103
PCT App. WO 97/41228
Pompon et al., *Meth. Enzymol.*, 272:51-64, 1996.
Potrykus et al., *Mol. Gen. Genet.*, 199:183-188, 1985.
Prasher et al., *Biochem. Biophys. Res. Commun.*, 126(3): 1259-1268, 1985.
Reichel et al., *Proc. Natl. Acad. Sci. USA*, 93 (12) p. 5888-5893. 1996.
Restrepo et al., *Plant Cell*, 2:987-998, 1990.
Ritala et al., *Plant Mol. Biol.*, 24(2):317-325, 1994.
Rogers et al., *Methods Enzymol.*, 153:253-277, 1987.

Sambrook et al., *In: Molecular Cloning-A Laboratory Manual* (second edition), Cold Spring Harbour Laboratory Press, 1989.
Schumacher et al., *Plant Cell Rep.*, 6:410-413, 1987.
Sheen et al., *Plant Journal*, 8(5):777-784, 1995.
Shimada et al., *Plant Sci.*, 160:37-47, 2000.
Simmonds and Stevenson, *J. Chem. Ecol.*, 27:965-977, 2001.
Singsit et al., *Transgenic Res.*, 6(2):169-176, 1997.
Stalker et al., *Science*, 242:419-422, 1988.
Sullivan et al., *Mol. Gen. Genet.*, 215(3):431-440, 1989.
Sutcliffe, *Proc. Natl. Acad. Sci. USA*, 75:3737-3741, 1978.
Tebayashi et al., *J. Exp. Bot.*, 52:681-668, 2001.
Thillet et al., *J. Biol. Chem.*, 263:12500-12508, 1988.
Thomas et al., *Plant Sci.* 69:189-198, 1990.
Thompson et al., *Euphytica*, 85(1-3):75-80, 1995.
Thompson et al., *The EMBO Journal*, 6(9):2519-2523, 1987.
Tian, Sequin, Charest, *Plant Cell Rep.*, 16:267-271, 1997.
Tingay et al., *The Plant Journal* v. 11 (6) p. 1369-1376. 1997.
Tolleson et al., *J. Agric. Food Chem.*, 50:4783-4790, 2002.
Tomes et al., *Plant. Mol. Biol.* 14(2):261-268, 1990.
Torbet, Rines, Somers, *Crop Science*, 38(1):226-231, 1998.
Torbet, Rines, Somers, *Plant Cell Reports*, 14(10):635-640, 1995.
Toriyama et al., *Theor Appl. Genet.*, 73:16, 1986.
Tsukada; Kusano; Kitagawa, *Plant Cell Physiol.*, 30(4) 599-604, 1989.
Twell et al., *Plant Physiol* 91:1270-1274, 1989.
Van Eck; Blowers; Earle, *Plant Cell Reports*, 14(5):299-304, 1995.
Vasil et al., *Plant Physiol.*, 91:1575-1579, 1989.
Walker et al., *Proc. Natl. Acad. Sci. USA*, 84:6624-6628, 1987.
Wang et al., *Molecular and Cellular Biology*, 12(8):3399-3406, 1992.
Wong, In: *The Flavonoids. Part 2*, Harborne et al. (Eds.), New York, San Francisco: Academic Press, 743-800, 1975.
Yamada et al., *Plant Cell Rep.*, 4:85, 1986.
Yang and Russell, *Proc. Natl. Acad. Sci. USA*, 87:4144-4148, 1990.
Zheng and Edwards, *J. Gen. Virol.*, 71:1865-1868, 1990.
Zukowsky et al., Proc. Natl. Acad. Sci. USA, 80:1101-1105, 1983.

What is claimed is:

1. An isolated nucleic acid sequence encoding a plant isoflavone 2'-hydroxylase, wherein the nucleic acid sequence is selected from the group consisting of:
   (a) a nucleic acid sequence encoding the polypeptide of SEQ ID NO:2;
   (b) a nucleic acid sequence comprising the sequence of SEQ ID NO:1;
   (c) a nucleic acid sequence hybridizing to SEQ ID NO:1 under conditions of 0.15 M NaCl and 70° C.;
   (d) a nucleic acid sequence comprising at least 90% sequence identity over the full length the nucleic acid sequence of SEQ ID NO:1; and
   (e) a nucleic acid sequence complementary to the nucleic acid sequence of polynucleotide sequence of (a), (b), (c) or (d).

2. A recombinant vector comprising the isolated polynucleotide of claim 1 operably linked to a heterologous promoter.

3. The recombinant vector of claim 2, further comprising at least one additional sequence chosen from the group consisting of: a regulatory sequence, a selectable marker, a leader sequence and a terminator.

4. The recombinant vector of claim 3, wherein the additional sequence is a heterologous sequence.

5. The recombinant vector of claim 2, wherein the promoter is a developmentally-regulated, organelle-specific, inducible, tissue-specific, constitutive, cell-specific, seed specific, or germination-specific promoter.

6. The recombinant vector of claim 2, defined as an isolated expression cassette.

7. A transgenic plant transformed with the recombinant vector of claim 2.

8. The transgenic plant of claim 7, further defined as a monocotyledonous plant.

9. The transgenic plant of claim 7, further defined as a dicotyledonous plant.

10. The transgenic plant of claim 7, further defined as a legume.

11. The transgenic plant of claim 7, further defined as an $R_0$ transgenic plant.

12. The transgenic plant of claim 7, further defined as a progeny plant of any generation of an $R_0$ transgenic plant, wherein said transgenic plant has inherited said selected DNA from said $R_0$ transgenic plant.

13. A seed of the transgenic plant of claim 7, wherein said seed comprises said selected DNA.

14. A host cell transformed with the recombinant vector of claim 2.

15. The host cell of claim 14, wherein said host cell is a plant cell.

16. A method of increasing disease resistance in a plant, comprising introducing into said plant the recombinant vector of claim 2, wherein the nucleic acid sequence encoding isoflavone 2'-hydroxylase is expressed to increase disease resistance in the plant relative to a plant of the same genotype lacking the nucleic acid sequence.

17. The method of claim 16, wherein the recombinant vector is inherited from a parent plant of said plant.

18. The method of claim 16, wherein the plant is directly transformed with the recombinant vector.

* * * * *